(12) United States Patent
Hingston et al.

(10) Patent No.: US 10,543,379 B2
(45) Date of Patent: Jan. 28, 2020

(54) RADIOACTIVE STENTS

(71) Applicant: BOSTON SCIENTIFIC SCIMED, INC., Maple Grove, MN (US)

(72) Inventors: John A. Hingston, Framingham, MA (US); Claude O. Clerc, Marlborough, MA (US); Daniel Ross, Watertown, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 257 days.

(21) Appl. No.: 15/297,245

(22) Filed: Oct. 19, 2016

(65) Prior Publication Data
US 2017/0113064 A1    Apr. 27, 2017

Related U.S. Application Data

(60) Provisional application No. 62/245,816, filed on Oct. 23, 2015.

(51) Int. Cl.
A61F 2/82    (2013.01)
A61N 5/10    (2006.01)

(52) U.S. Cl.
CPC .............. *A61N 5/1027* (2013.01); *A61F 2/82* (2013.01); *A61F 2210/0095* (2013.01); *A61N 2005/1019* (2013.01); *A61N 2005/1024* (2013.01)

(58) Field of Classification Search
CPC ............................................. A61F 2210/0095
See application file for complete search history.

(56) References Cited

U.S. PATENT DOCUMENTS

| | | | |
|---|---|---|---|
| 5,213,561 A * | 5/1993 | Weinstein | A61N 5/1002 600/3 |
| 5,713,828 A | 2/1998 | Coniglione | |
| 5,891,108 A | 4/1999 | Leone et al. | |
| 6,159,143 A | 12/2000 | Lennox | |
| 6,192,271 B1 * | 2/2001 | Hayman | A61N 5/1002 604/21 |
| 6,402,736 B1 | 6/2002 | Brown et al. | |

(Continued)

FOREIGN PATENT DOCUMENTS

| | | |
|---|---|---|
| DE | 19913978 A1 | 9/2000 |
| WO | 9848851 A2 | 11/1998 |

(Continued)

OTHER PUBLICATIONS

Gaspar et al., "American Brachytherapy Society (ABS) Consensus Guidlines for Brachytherapy of Esophageal Cancer", Int. J. Radiation Oncology Biol. Phys., vol. 38(1): 127-132, Apr. 1, 1997.

(Continued)

*Primary Examiner* — Jacqueline Woznicki
(74) *Attorney, Agent, or Firm* — Seager, Tufte & Wickhem, LLP

(57) ABSTRACT

This disclosure provides design, material, manufacturing method, and use alternatives for medical devices. An example medical device includes a stent having a first strut. The first strut may include an inner surface and an outer surface. The medical device may also include a first attachment member coupled to the strut and a radioactive element. The radioactive element may be coupled to the attachment member.

20 Claims, 23 Drawing Sheets

(56) References Cited

U.S. PATENT DOCUMENTS

| | | |
|---|---|---|
| 6,524,232 B1 | 2/2003 | Tang et al. |
| 6,537,193 B1 | 3/2003 | Lennox |
| 6,582,353 B1 | 6/2003 | Hastings et al. |
| 6,599,230 B2 | 7/2003 | Hastings et al. |
| 6,638,205 B1 | 10/2003 | Chan et al. |
| 6,716,156 B2 | 4/2004 | Menuhr et al. |
| 6,918,869 B2 | 7/2005 | Shaw et al. |
| 7,074,291 B2 | 7/2006 | Terwillinger et al. |
| 7,252,630 B2 | 8/2007 | Terwillinger et al. |
| 7,344,490 B2 | 3/2008 | Shaw et al. |
| 7,351,192 B2 | 4/2008 | Elliott et al. |
| 7,887,476 B2 | 2/2011 | Hermann et al. |
| 8,114,007 B2 | 2/2012 | Lamoureux et al. |
| 8,298,129 B2 | 10/2012 | Elliott et al. |
| 2001/0001112 A1 | 5/2001 | Hayman |
| 2001/0032013 A1* | 10/2001 | Marton ............... A61F 2/91 623/1.15 |
| 2002/0133220 A1 | 9/2002 | Lundqvist |
| 2002/0193655 A1 | 12/2002 | Candelaria et al. |
| 2004/0116767 A1 | 6/2004 | Lebovic et al. |
| 2004/0225176 A1 | 11/2004 | Flanagan et al. |
| 2006/0241741 A1* | 10/2006 | Lootz ................ A61F 2/91 623/1.34 |
| 2007/0270627 A1 | 11/2007 | Cutrer et al. |
| 2008/0071132 A1 | 3/2008 | Lamoureux et al. |
| 2009/0076588 A1 | 3/2009 | Weber |
| 2009/0093668 A1 | 4/2009 | Marten et al. |
| 2009/0326314 A1 | 12/2009 | Cutrer et al. |
| 2010/0030127 A1 | 2/2010 | Liu et al. |
| 2010/0137673 A1 | 6/2010 | Srivastava et al. |
| 2015/0190654 A1 | 7/2015 | Herskovic |

FOREIGN PATENT DOCUMENTS

| | | |
|---|---|---|
| WO | 9961107 A1 | 12/1999 |
| WO | 0136007 A2 | 5/2001 |
| WO | 02049535 A2 | 6/2002 |
| WO | 03037397 A2 | 5/2003 |
| WO | 2007082189 A2 | 7/2007 |

OTHER PUBLICATIONS

Langley et al., "4D Brachytherapy, a novel real-time prostate brachytherapy technique using stranded and loose seeds", BJU International, vol. 109, Supplement 1, 1-9, Feb. 2012.

Lendlein et al., "Shape-Memory Polymers", Angew. Chem. Int. Ed., vol. 41(12):2034-2057, Jun. 17, 2002.

Talreja et al., "Fully covered removable nitinol self-expandable metal stents (SEMS) in malignant strictures of the esophagus: a multicenter analysis", Surg. Endosc., vol. 26(6):1664-1669, Jun. 2012.

U.S. Appl. No. 15/237,270, filed Aug. 15, 2016, "Radioactive Stent."

U.S. Appl. No. 15/237,147, filed Aug. 15, 2016, "Radioactive Stent."

U.S. Appl. No. 14/629,067, filed Feb. 23, 2015, "Device and Method for Improving Brachytherapy."

* cited by examiner

RADIOACTIVE STENTS

CROSS-REFERENCE TO RELATED APPLICATIONS

This application claims priority under 35 U.S.C. § 119 to U.S. Provisional Application Ser. No. 62/245,816, filed Oct. 23, 2015, the entire disclosure of which is incorporated herein by reference

TECHNICAL FIELD

The present disclosure pertains to medical devices, and methods for manufacturing medical devices. More particularly, the present disclosure pertains to elongated intracorporeal medical devices including an attachment member connected with other structures, and methods for manufacturing and using such devices.

BACKGROUND

Some cancers and neoplasms are easier to treat with radiation than others. Hard-to-reach neoplasms, such as those in the esophagus, intestines and other lumens, may be treated via Brachytherapy so as to minimize radiation to adjacent, healthy tissue.

Brachytherapy delivers radiation to small tissue volumes while limiting exposure of healthy tissue. In this regard, the delivered radiation conforms more to the target than any other form of radiation, (including proton therapy) as less normal transient tissue is treated. It features placement of radiation sources, such as small radioactive particles or needles, near or within the target tissue, thus having the advantage over External Beam Radiation Therapy (EBRT) of being more focalized and less damaging to surrounding healthy tissue.

Brachytherapy is a common treatment for esophageal, prostate, and other cancers. Brachytherapy has been used to treat prostate cancer which has been practiced for more than half century. In this situation, very low activity material emitting a low energy is placed next to or within a tumor. Traditionally, these low emitting devices have mostly been left in place permanently except in extraordinary circumstances. It would be desirable to utilize radioactive material in conjunction with interventional medical devices when clinically appropriate, and/or it may be desirable to tailor the delivery of radioactive energy or radioactive sources according to clinical needs. For example, it may be advantageous to couple a radiation source with an expandable stent when clinically necessary and/or it may be advantageous to adjust the position and the activity of the radioactive source on a stent in response to changes in tumor shape and size, carrier position, and other relevant therapeutic factors.

BRIEF SUMMARY

This disclosure provides design, material, manufacturing method, and use alternatives for medical devices. An example medical device comprises a stent including a first strut having an inner surface and an outer surface. The device also includes a first attachment member coupled to the first strut, and a radioactive element coupled to the first attachment member.

Alternatively or additionally to any of the embodiments above, the radioactive element further comprises an axially elongated radioactive seed.

Alternatively or additionally to any of the embodiments above, the first attachment member includes a base, a first grip member and a second grip member, wherein the first and second grip members extend away from the base member.

Alternatively or additionally to any of the embodiments above, the radioactive element is positioned between the first and second grip members.

Alternatively or additionally to any of the embodiments above, the radioactive element is positioned radially outward from the base member.

Alternatively or additionally to any of the embodiments above, the first and second grip members are configured to compress the radioactive element against the base member.

Alternatively or additionally to any of the embodiments above, the stent further comprises a second strut longitudinally spaced from the first strut, and the first attachment member is positioned between the first strut and the second strut.

Alternatively or additionally to any of the embodiments above, further comprising a first connector having a first end coupled to the first attachment member and a second end coupled to the first strut, and wherein the first connector spaces the first attachment member longitudinally away from the first strut.

Alternatively or additionally to any of the embodiments above, further comprising a second connector having a first end coupled to the first attachment member and a second end coupled to the second strut, and wherein the second connector spaces the attachment member longitudinally away from the second strut.

Alternatively or additionally to any of the embodiments above, further comprising a second attachment member.

Alternatively or additionally to any of the embodiments above, the radioactive element includes a radioactive strand, and wherein the radioactive strand extends from the first attachment member to the second attachment member.

Alternatively or additionally to any of the embodiments above, the first attachment member includes a loop portion extending away from the outer surface of the stent, wherein the loop portion includes an aperture having an axis substantially parallel to a longitudinal axis of the stent, and wherein the radioactive element is positioned within the aperture of the loop portion.

Alternatively or additionally to any of the embodiments above, further comprising a radioactive shield, wherein the radioactive shield is configured to modulate radioactive energy released from the radioactive element.

Alternatively or additionally to any of the embodiments above, the first attachment member extends radially inward from the inner surface of the stent.

Alternatively or additionally to any of the embodiments above, wherein the first attachment member includes an outwardly extending strut, and wherein the radioactive element is positioned between the first strut and the outwardly extending strut.

Another example medical device comprises a stent including a monolithic tubular scaffold. The scaffold includes a plurality of integrally formed struts defining one or more interstices therebetween. The medical device further comprises a gripping member coupled to the monolithic scaffold and a radioactive element disposed along the gripping member.

Alternatively or additionally to any of the embodiments above, further comprising a second gripping member, and wherein the second gripping member is circumferentially spaced from the first gripping member.

Alternatively or additionally to any of the embodiments above, wherein the radioactive element includes a radioactive seed, a radioactive strand, or both.

Alternatively or additionally to any of the embodiments above, further comprising a radioactive shield, wherein the radioactive shield is configured to modulate radioactive energy released from the radioactive element.

Another example medical device comprises a stent having a first strut including an inner surface, an outer surface and a base. The medical device further includes a first attachment member formed from the base of the first strut, wherein the attachment member includes a first gripping portion and a second gripping portion. A radioactive element is positioned between the first and second gripping portions and the radioactive element extends radially outward from the base.

The above summary of some embodiments is not intended to describe each disclosed embodiment or every implementation of the present disclosure. The Figures, and Detailed Description, which follow, more particularly exemplify these embodiments.

BRIEF DESCRIPTION OF DRAWINGS

The disclosure may be more completely understood in consideration of the following detailed description in connection with the accompanying drawings, in which.

Figure 1A:
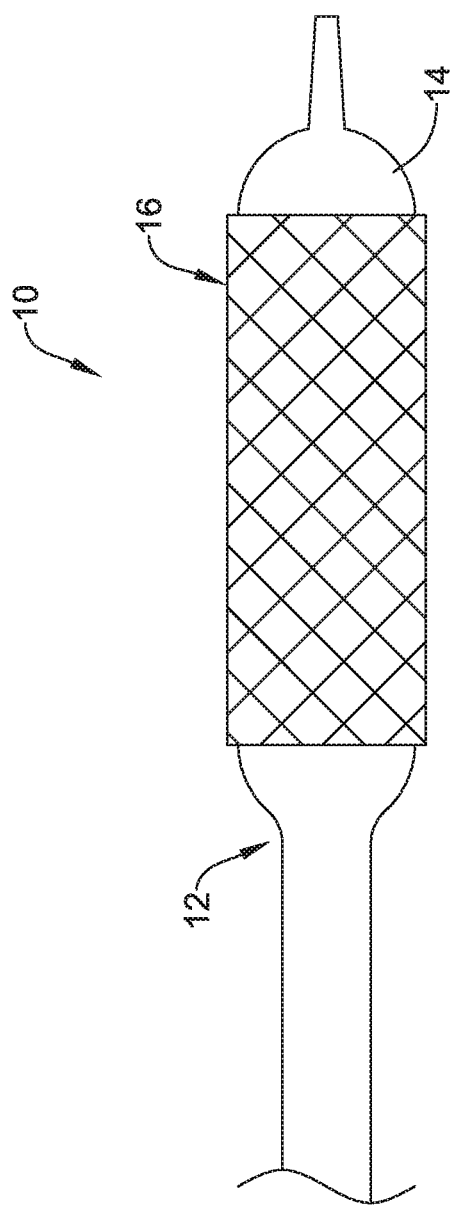
FIG. 1A is an example stent and stent delivery device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Treatment of abnormal tissue growth (e.g. cancer) may be accomplished through a variety of methodologies. For example, treatment of cancer may include the placement and deployment of a stent across the diseased tissue. However, in some instances stenting outcomes may be improved by combining one or more conventional therapies. For example, combining stent placement with radiation therapy may improve cancer treatment outcomes as compared to either stent or radiation therapy alone. Therefore, it may be desirable to utilize materials and/or design a stent that combines traditional stenting with radiation therapy. Some of the examples and methods disclosed herein may include a stent that can deliver radiation therapy.

Stents disclosed herein may treat esophageal cancers. Additionally, the stent may treat other forms of disease, including gastrointestinal, airway, urethra, ureter, cardiac, brain, breast, bladder, kyphoplasty and peripheral vascular disease, for example. Further, the stents disclosed herein may also be used in excisional cavities in solid and/or hollow organs.

FIG. 1A shows an example radioactive stent system 10. Stent system 10 may include a stent 16. Stent 16 may be delivered to a treatment area via a stent delivery system 12. For example, stent 16 may be disposed on an expandable member 14.

In some instances stent 16 may be a balloon expandable stent. Balloon expandable stents may be manufactured from a single, cylindrical tubular member. For example, in some instances, a cylindrical tubular member may be laser cut to form balloon expandable stent 16.

Figure 1B:
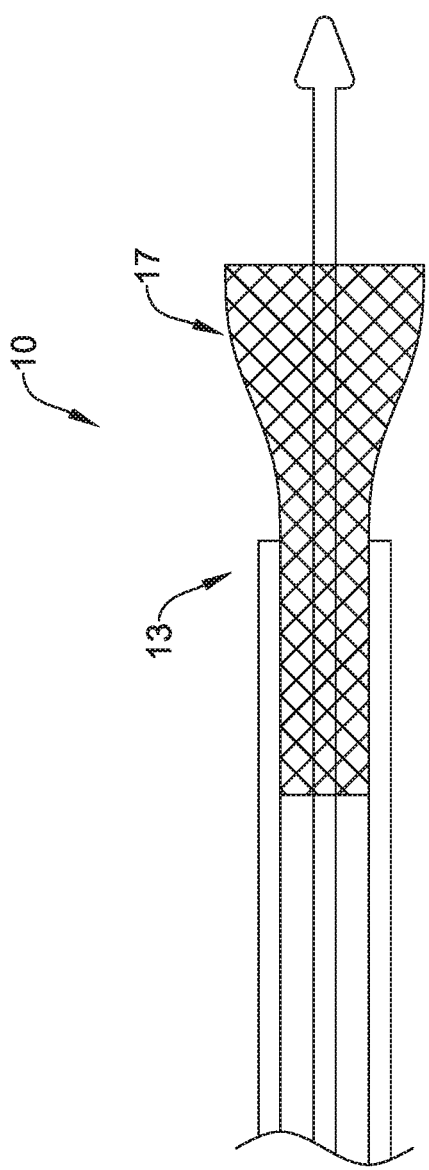
FIG. 1B is another example stent and stent delivery device.

In other instances stent system 10 may include a self-expanding stent. For example, FIG. 1B shows another example radioactive stent system 10. Stent system 10 may include a self-expanding stent 17. Self-expanding stent 17 may be delivered to a treatment area via a self-expanding stent delivery system 13. It is contemplated that the examples disclosed herein may be utilized with any one of various stent configurations, including, balloon expandable stents, such as a laser cut stent and/or a braided stent, a self-expanding stent, non-expandable stents, or other stents.

Stent 16 disclosed herein may be constructed from a variety of materials. For example, stent 16 may be constructed from a metal (e.g., Nitinol). In other instances, stent 16 may be constructed from a polymeric material (e.g., PET). In yet other instances, stent 16 may be constructed from a combination of metallic and polymeric materials. Additionally, stent 16 may include a bioabsorbable and/or biodegradable material.

Stent 16 may include a covering. For example, stent 16 may be partially or fully covered by an elastomeric or non-elastomeric material. Additionally, stent 16 may be partially or fully covered by a polymeric material such as silicone or ePTFE. Further, the covering (e.g., polymer) may span the spaces (e.g., openings, cells) in the wall of stent 16.

Figure 2:
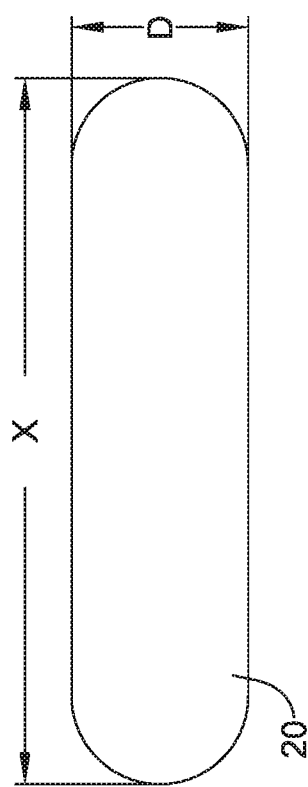
FIG. 2 is an example radioactive element.

FIG. 2 shows an example radioactive element 20. In some instances, radioactive element 20 may be referred to as a "seed." The terms "radioactive element" and "seed" may be used interchangeably throughout the remainder of this discussion. In general, seed 20 may be positioned adjacent a target site, whereby seed 20 may release radioactive energy and/or material, thereby radioactively treating the target location.

Seed 20 may be generally shaped as shown in FIG. 2. In other words, seed 20 may be an elongated cylinder having rounded ends. However, other shapes are contemplated. For example, seed 20 may be rounded, ovular, rectangular, triangular, or the like.

FIG. 2 shows the length of seed 20 depicted as dimension "X" and the diameter of seed 20 as dimension "D." Depending on the particular therapeutic application, different types of seeds may have different dimensions. For example, in some instances, seed 20 may have a length "X" of between 1 and 20 mm. In other examples, seed 20 may have a length "X" between 2 and 10 mm, or between 3 and 8 mm. In some examples, seed 20 may have a length of about 5 mm.

Additionally, in some instances, seed 20 may have a diameter "D" of between 0.1 and 1.5 mm. In other examples, seed 20 may have a diameter "D" between 0.2 and 1 mm, or between 0.3 and 0.8 mm. In some examples, seed 20 may have a diameter of about 0.5 mm.

Seed 20 may include a variety of radioactive materials and or combinations of various materials. For example, seed 20 may include Iodine-125 (e.g. GE Oncura THINSeed™, IsoAid Advantage™ by IsoAid, Best™ Iodine-125), Palladium-103 (e.g. CivaString™ by CivaTech Technology, Theraseed™ by Theragenics, Best™ Palladium-103), Cesium-131, Gold-198, Iridium-192 and/or Ytterbium-169 or any other variations and/or derivatives thereof. Further, seed 20 may include other types of radioactive material. Additionally, seed 20 may include beta-emitting radionuclides.

Figure 3:
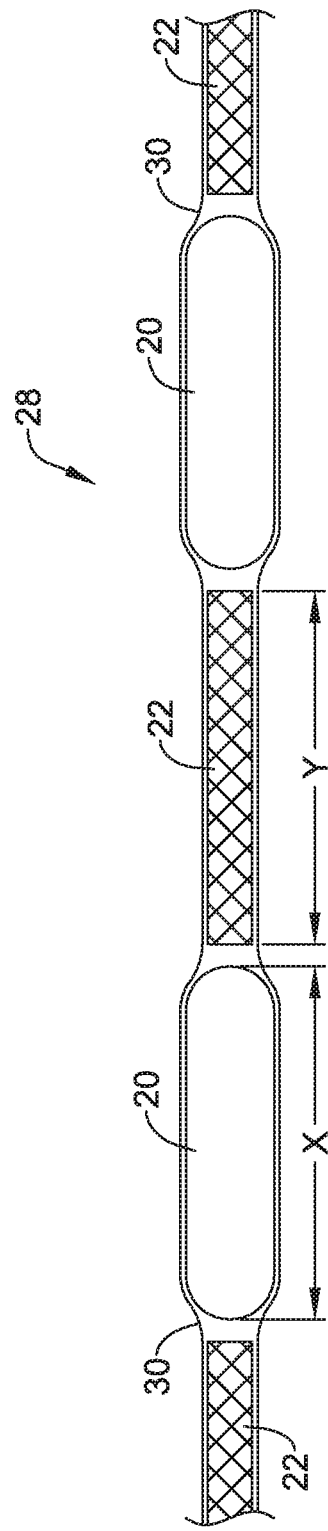
FIG. 3 is an example radioactive strand having radioactive seeds and spacers.

In some instances, one or more seeds 20 may combined with one or more additional seeds 20 and/or one or more spacing elements to form an elongated treatment member. For example, FIG. 3 shows elongated treatment member 28 including seeds 20 and spacing elements 22 positioned between adjacent seeds 20. In some instances (including the following discussion herein), treatment member 28 may be referred to as a "strand."

The example shown in FIG. 3 depicts a covering 30 surrounding the seeds 20 and spacers 22. In some instances, covering 30 may include a material capable of being placed over the combination of seeds 20 and/or spacers 22 to form a continuous strand 28. In some examples, covering 30 may include one or more of a variety of shrink tubing (e.g. a polymeric tubing capable of reducing in size upon the application or heat, for example). In other examples, the covering may include a bioabsorbable and/or biodegradable material. Additionally, in some instances seeds 20 and/or spacers 22 may be connected to one another via a bioabsorbable connector. In other words, a combination of seeds 20 and/or spacers 22 may be "linked" to one another by a bioabsorbable and/or biodegradable material. In some instances, the radioactive strand 28 may include a radioactive wire.

Seeds 20 and spacers 22 may be spaced and/or distributed in various patterns and/or distributions along strand 28. The length of the spacers 22 (which may correspond to the space between any two seeds 20) may vary depending on the particular strand 28 configuration. Similarly, the length of a given seed 20 in combination with a variety of lengths of given spacers 22 may vary depending on a particular strand 28 configuration. For example, FIG. 3 depicts the length of an example seed 20 as "X" and the spacing distance between seeds as "Y." In some example strands 28, the length "X" of the seed 20 may be between 2-8 mm, while the length "Y" of spacer 22 may be between 2-20 mm.

However, different lengths of the both seeds 20 and spacers 22 are contemplated. Further, it can be appreciated that while some examples depicted in the figures disclosed herein show each seed 20 separated by a spacer 22, in some stances one or more seeds 20 may be placed directly adjacent one another. For example, 2, 3, 4, 5, 6, 7, 8, 9, 10, 15, 20 or more seeds 20 may be placed adjacent one another in a given strand 28. Further, adjacently placed seeds 20 may be separated from other adjacently placed seeds 20 by any length spacer 22.

Additionally, a given seed 20 and a given spacer 22 may have different dimensions despite being positioned adjacent one another in a given strand 28. For example, a given strand 28 may have a variety of seeds 20 having a variety of different lengths, diameters, materials and activities. Similarly, a given strand 28 may have a variety of spacers 22 having a variety of different lengths, diameters and materials. Further, it is contemplated that a given strand 28 may combine seeds 20 and spacers 22 in a variety of different combinations, patterns, distributions, separations, arrangements, or the like depending on the particular strand design required for a particular therapeutic application or user preference, for example.

In some instances it may be desirable to combine seeds 20 and/or spacers 22 with stent 16 to form a stent system 10 having the structural elements of stent 16 combined with the therapeutic properties of a radioactive material (e.g., seeds 20 and/or strand 28). Further, in some instances it may be desirable to utilize a structural element that can both engage with the stent structure while also being capable of gripping (e.g., holding) the radioactive material (e.g., seeds 20 and/or strand 28).

Figure 4:
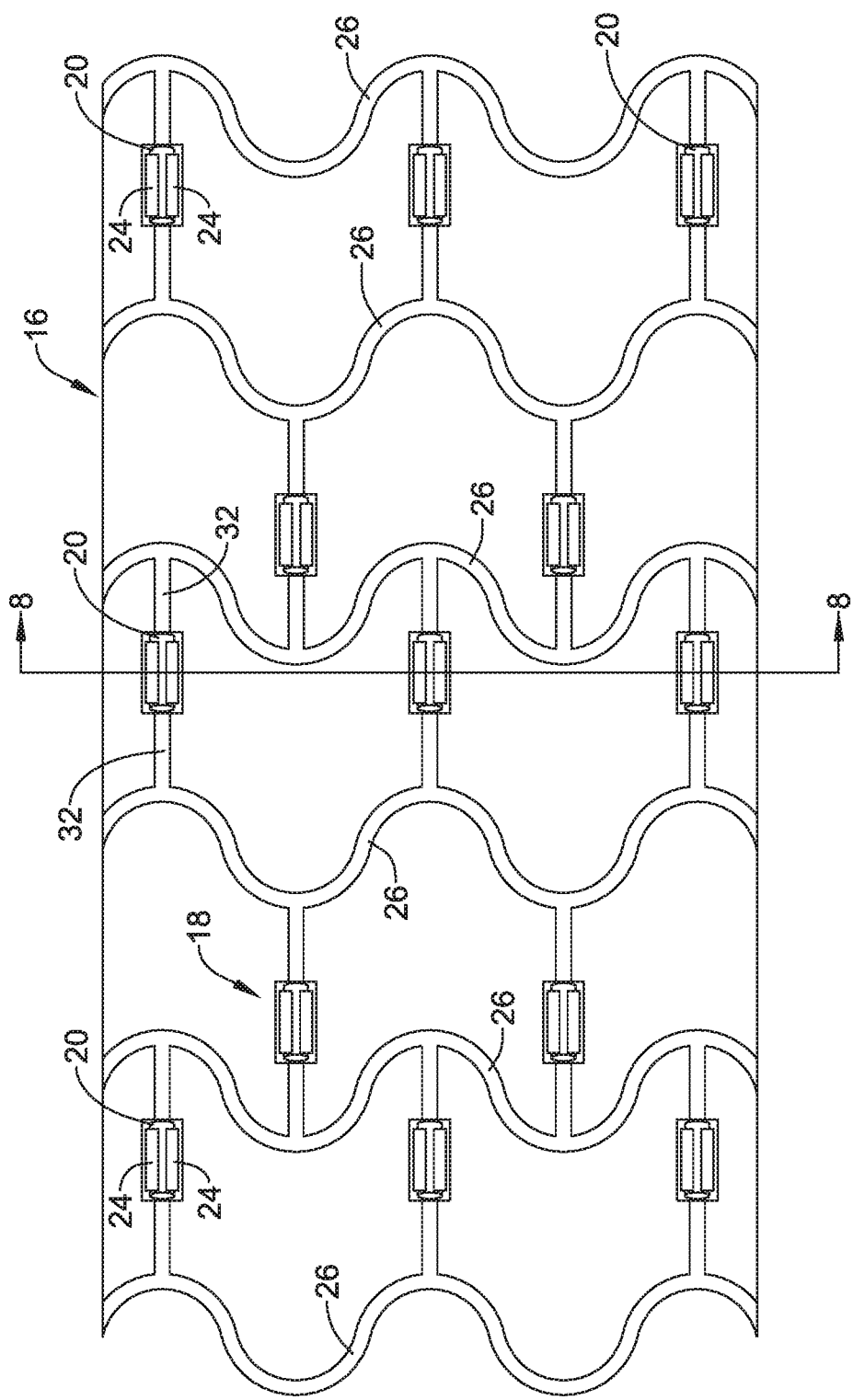
FIG. 4 is an example stent including radioactive elements.

FIG. 4 shows an example stent 16 including one or more attachment members 24 configured to accept, receive, grip, compress, hold and/or contain a radioactive element (e.g., seed 20). Stent 16 may include one or more struts 26 configured in various designs and/or patterns. For example, stent 16 may be a laser cut stent formed from a unitary tubular member. Therefore, numerous designs, patterns and/or configurations for the stent cell openings, strut thicknesses, strut designs, stent cell shapes are contemplated and may be utilized with embodiments disclosed herein.

Figure 7:
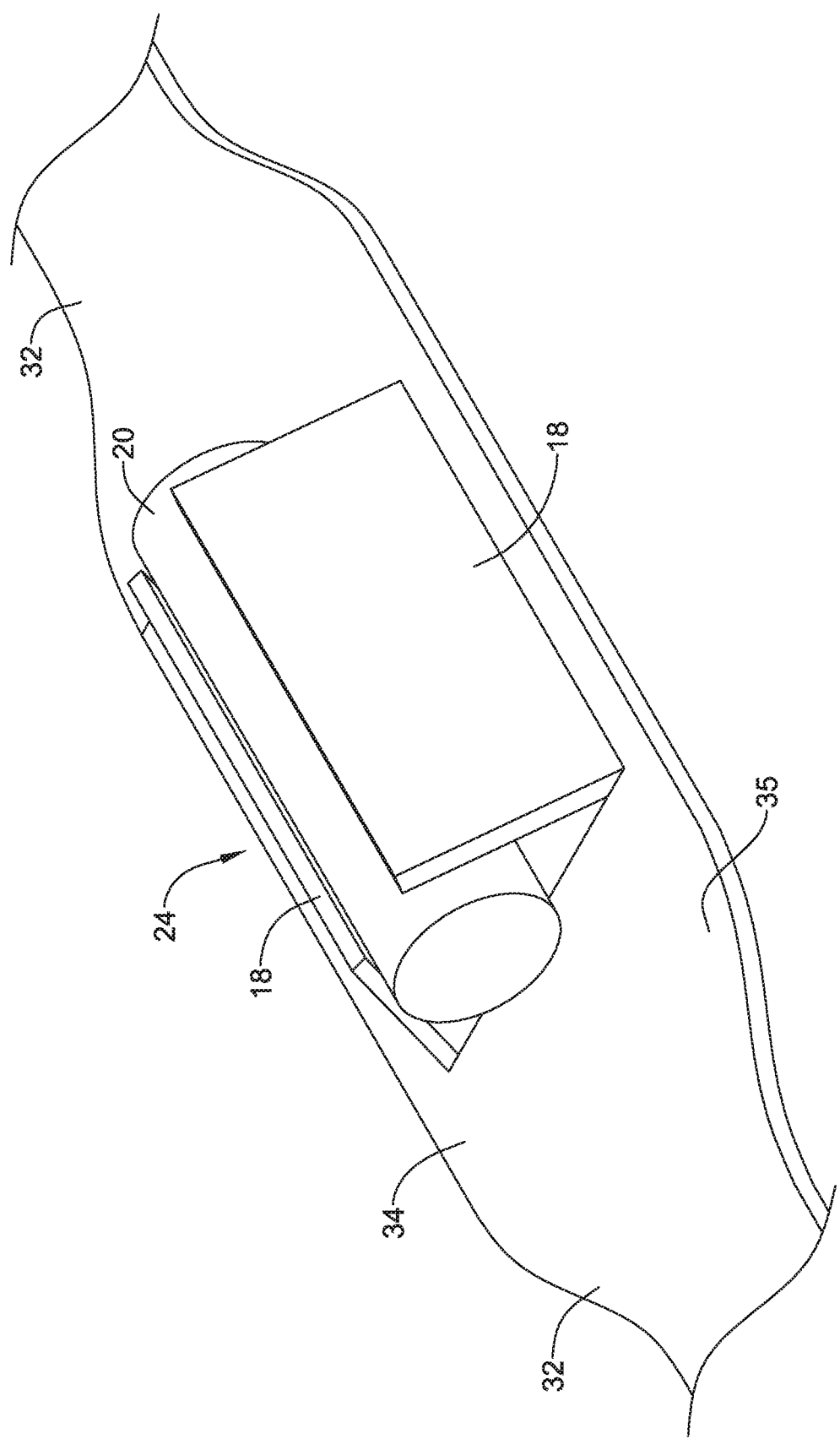
FIG. 7 is an example radioactive element coupled to an attachment member.

As shown in FIG. 4, attachment members 24 may be positioned between adjacent stent struts 26. In other words, in some examples attachment members 24 may be longitudinally spaced away from adjacent stent struts 26. For example, FIG. 4 shows example attachment members 24 connected to stent struts 26 via stent connectors 32. Connectors 32 may be coupled to and/or extend from the distal and/or proximal ends of attachment members 24. For the purposes of this disclosure, the term "coupled" may refer to instances in which an attachment member is a separate component connected, releasably attached, bonded, secured, welded, affixed, etc. to adjacent structures (e.g., such as a structural component of the stent, as shown in FIG. 4), but also includes instances in which an attachment member may be integral with or monolithically formed as a unitary portion of a structural component of the stent, such as from the tubular member from which the stent is constructed (e.g., formed unitarily with a strut and/or strut connector of the stent, as shown in FIG. 7).

FIG. 4 shows attachment members 24 aligned along the longitudinal axis of stent 16. In other words, attachment members 24 may be generally rectangular in shape and aligned such that their length is aligned with the longitudinal axis of stent 16. Further, attachment members 24 may be distributed about the circumference of stent 16. For example, in some examples attachment members 24 may be generally spaced equidistant from one another along the circumference of stent 16. However, in other examples, attachment members 24 may be spaced in a variety of configurations circumferentially or longitudinally along stent 16.

Figure 5:
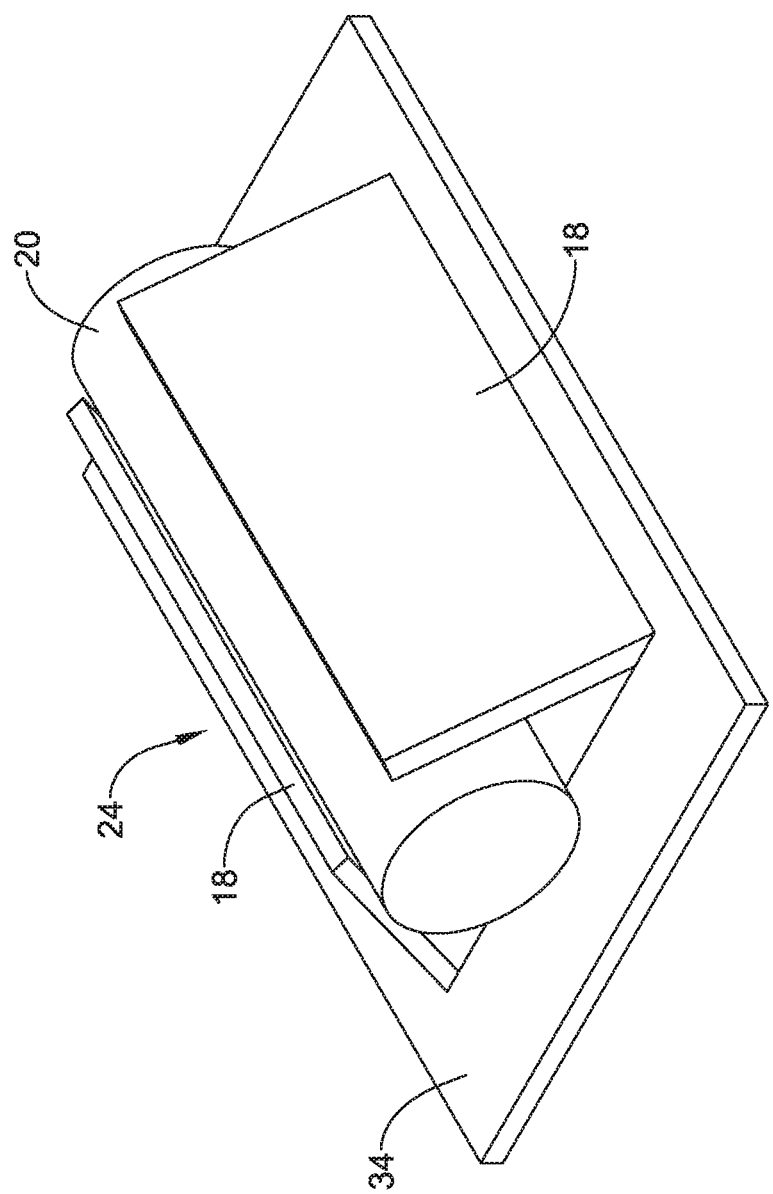
FIG. 5 is an example radioactive element coupled to an attachment member.

FIG. 5 shows example seed 20 coupled (e.g., releasably attached) to an attachment member 24. Attachment member 24 may include first and second arms or sides 18 and a base portion 34. As shown in FIG. 5, arms or sides 18 may extend radially away from base portion 34. In other words, arms or sides 18 may pivot or bend outward (e.g., away from) from the outer surface (e.g. outer surface of stent 16) of base member 34. Further, arms or sides 18 may pivot or bend through any angle with respect to base member 34. For example, FIG. 5 shows arms or sides 18 being positioned at approximately a 45 degree angle with respect to the outer surface of base member 34. However, it may be desirable for arms or sides 18 to be positioned at any angle (e.g., approximately 0 to 90 degrees) with respect to the outer surface of base member 34. In some examples, arms or sides 18 may be 0.2-1.5 mm long, or about 0.4-0.8 mm long, or approximately 0.6 mm long, for instance.

Figure 6:
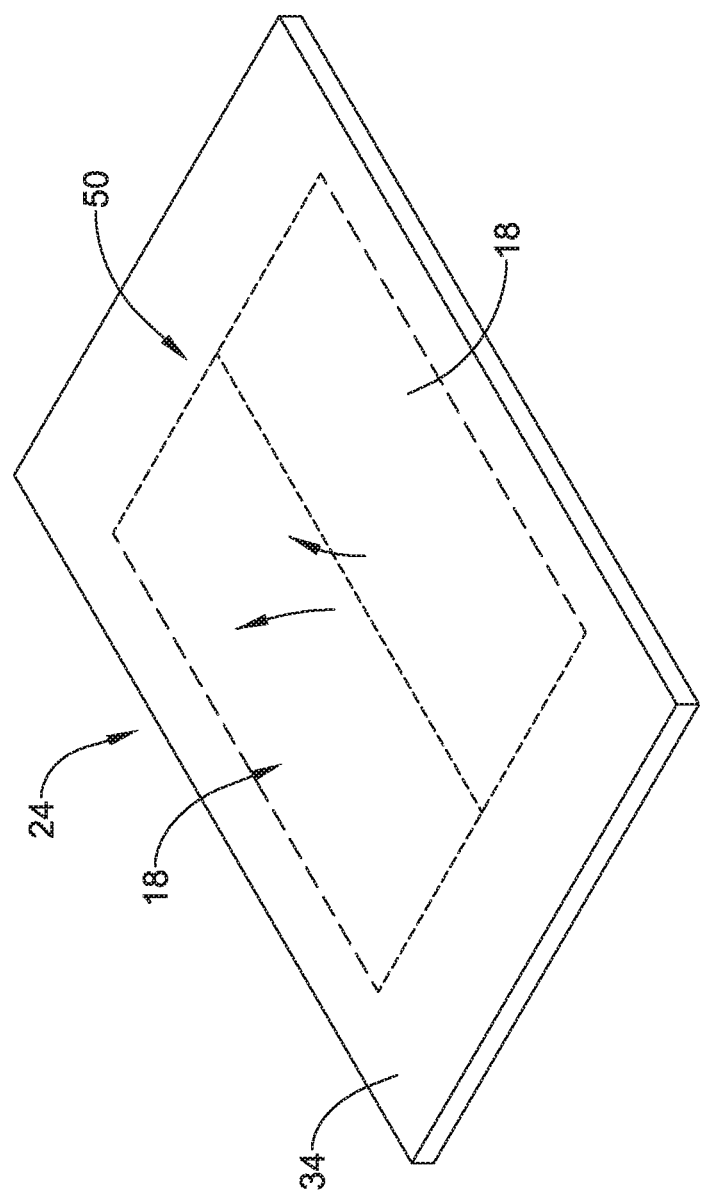
FIG. 6 is an example stent strut including example cutting lines.

Arms or sides 18 may be formed from base 34, or formed separately and subsequently secured to base 34. For example, it can be appreciated that base member 34 may be cut using a suitable process (e.g., laser cutting) to form the two arms or sides 18 shown FIG. 5. For example, FIG. 6 illustrates an example pattern which may be laser cut to form the arms or sides 18 shown in FIG. 5. In some methods, a laser may cut through base member 34 along cut lines 50 (illustrated as dashed lines in FIG. 6). Once cut lines 50 along base member 34 have been cut, arms or sides 18 may be bent or deflected (e.g., "folded") radially outward (illustrated by curved arrows in FIG. 6) from base member 34 to form the structure of attachment member 24 shown in FIG. 5.

In some instances, after base portion 34 has been cut along example cut lines 50, stent 16 may be expanded (e.g., from its initial tube state) to an expanded state. A heat set may then be applied. After the heat set, stent 16 may be placed over a mandrel designed to open or bend arms or sides 18, thereby forming attachment member 24. The example stent 16 may then be heat set a second time.

FIG. 5 further illustrates example seed 20 coupled to attachment member 24. As shown, seed 20 may be positioned between arms or sides 18 and/or base member 34. Placement of seed 20 between arms or sides 18 may deflect arms or sides 18 away from an equilibrium position, such that arms or sides 18 press against seed 20 positioned therebetween. Arms or sides 18 may compress radioactive element 20 therebetween and/or against base 34. In some examples, arms or sides 18 may function to pinch, hold, retain and/or grip radioactive element 20 such that radioactive element is coupled (e.g., releasably attached) to stent 16. In some examples, after radioactive element 20 is positioned between arms or sides 18, arms or sides 18 may be biased toward base portion 34 such that seed 20 is unable to move (e.g., slide) relative to base 34 and/or stent 16.

While the above descriptions show attachment members 24 being generally rectangular with a length aligned along the longitudinal axis of stent 16, it is contemplated that attachment members 24 may be of any shape and may be aligned in any pattern along stent 16. For example, attachment members 24 may be square, circular, ovular, polygonal, triangular or the like.

Further, in some instances attachment member 24 may be defined as a separate member that is attached to stent 16, stent connector 32 and/or stent strut 26. For example, attachment member 24 may be defined as a clip that is attached or secured (e.g., welded) to stent strut 26. However, in other instances attachment member 24 may be formed (e.g., laser cut) directly from a stent strut 26. In other words, attachment member 24 may be defined as being a unitary or integral component of the tubular member forming the stent 16.

FIG. 7 shows attachment member 24 being formed integrally from example stent strut connector 32. As shown in FIG. 7, attachment member 24 is generally equivalent to the attachment members 24 as depicted and described with respect to FIG. 5. However, FIG. 7 shows attachment member 24 (including sides 18) formed from stent strut connector 32. It is contemplated that any portion of stent 16 may be utilized to create an attachment member 24 at any point along stent 16, such as a portion of a stent strut 26. Additionally, stent 16 may include a combination of attachment members 24 formed integrally with stent struts 26 and/or strut connectors 32, and/or as separate attachment members 24 coupled to stent 16 in a separate process (e.g., welded to stent 16).

Figure 8:
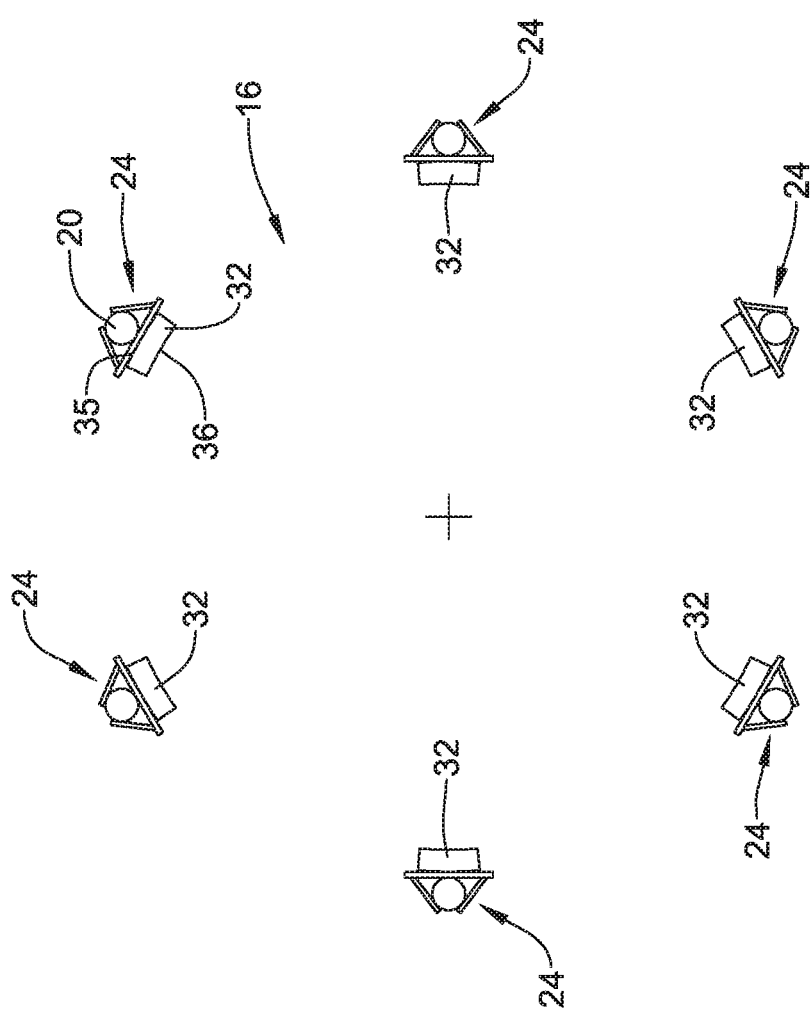
FIG. 8 is a cross section of example radioactive elements coupled to a stent.

FIG. 8 illustrates a cross sectional view of stent 16 along line 8-8 of FIG. 4. As shown in FIG. 8, the cross sectional view of stent 16 shows six attachment members 24 coupled to stent strut connectors 32. It can be appreciated from FIG. 8 that each stent strut connector 32 includes an inner surface 36 and an outer surface 35. FIG. 8 further illustrates that attachment members 24 may be coupled to the outer surface 35 of stent strut connectors 32. When coupled to the outer surface 35 of stent strut connectors 32, the attachment members 24 (and, therefore, seeds 20), may extend radially outward from the outer surface 35 of stent strut connectors 32. While FIG. 8 may depict attachment members 24 as being separate elements coupled to the outer surface 35 of stent strut connectors 32, it is contemplated that attachment member 24 may be formed integrally with stent strut connectors 32 (as shown in FIG. 7). In both examples, radioactive elements 20 may extend radially outward from stent 16.

Additionally, while FIG. 8 depicts six attachment members 24 positioned substantially equidistant around the circumference of stent 16, it is contemplated that more or fewer than six attachment members 24 may be coupled to stent 16. For example, stent 16 may include 1, 2, 3, 4, 5, 6, 7, 8, 9, 10, 11, 12, 13, 14, 15, 20, 25, 30, 40, 50 or more attachment members coupled to stent 16. As discussed above, the attachment members 24 may be distributed, arranged and/or positioned in a variety of patterns or distributions along stent 16.

In some instances it may be favorable to ensure that the radioactive elements 20 are positioned radially inward from stent 16 in order to minimize the occurrence of "hot spots" at the tissues contacting the stent near radioactive elements 20. This may be accomplished by positioning the radioactive elements inside stent 16. For instance, while not shown in the figures, in some examples attachment members 24 (including sides 18 and seed 20) may extend radially inward from inner surface 36 of stent 16. Further, attachment members 18 may be coupled to the inner surface 36 of stent strut connector 32 and/or strut 26 or may be integrally formed with stent strut connector 32 and/or strut 26.

In some instances it may be desirable to direct radioactive energy to a specific portion of a target area (e.g., a particular portion of a target vessel). Creating variations in the delivery of radioactive energy may be accomplished by changing both structural elements of the stent system and/or the spacing between the structural elements. For example, increasing the number of radioactive elements engaged to a given stent may result a more dense number of radioactive elements for a given circumferential surface of a stent. Furthermore, it can be appreciated that an increased density may result from increasing the total number of radioactive elements in a given stent. In some instances, the distribution of radioactive elements along a stent may be such that the tissue surrounding stent may receive a substantially uniform amount of radioactive energy. In other instances, radioactive elements may be asymmetrically arranged about a stent such that a concentrated amount of radiation is delivered to a specific target tissue location. For example, an asymmetrically shaped tumor may require an asymmetrical distribution of radioactive elements (and therefore, a non-uniform distribution of radioactive elements) configured to deliver a customized dose of radiation to the tissue of the asymmetrical tumor.

Figure 9:
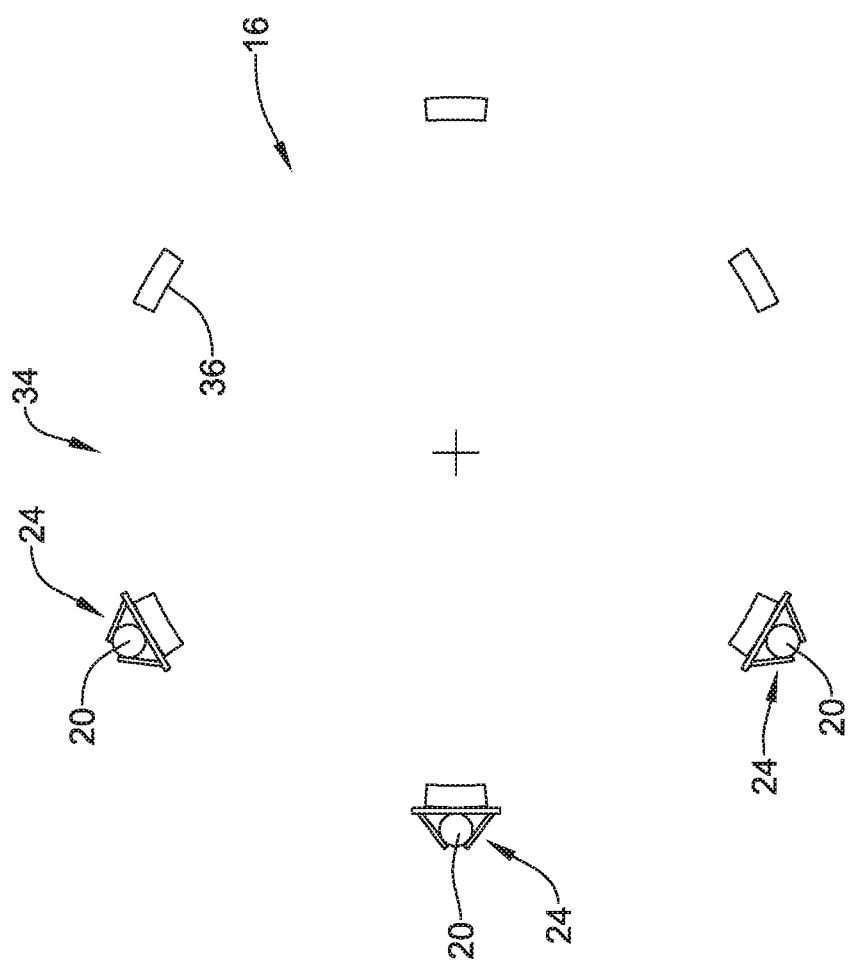
FIG. 9 is a cross section of example radioactive elements coupled to a stent.

For example, in some instances it may be desirable to direct radioactive energy away from only one portion of stent 16. In some examples, this may include positioning radioactive elements 20 asymmetrically about the circumference of stent 16. FIG. 9 illustrates stent 16 including radioactive elements 20 positioned on only a first portion of a circumference of stent 16 (on one side of stent 16) while the remaining portion of circumference of stent 16 (the other side of stent 16) is devoid of radioactive elements 20. As shown, three attachment members 24 are positioned on one side of stent 16. While FIG. 9 shows a three attachment members positioned adjacent one another, any distribution and/or arrangement of attachment members 24 around the circumference of stent 16 is contemplated.

Figure 10:
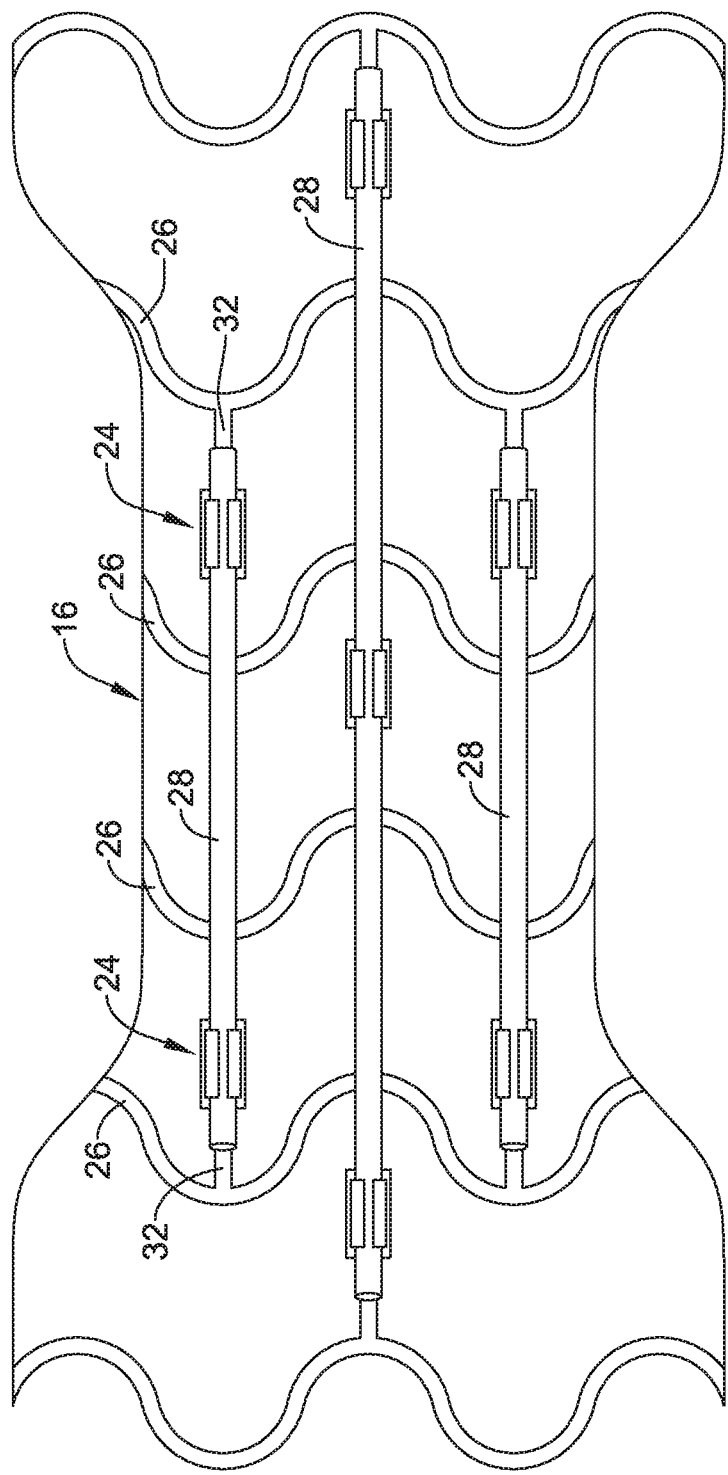
FIG. 10 is an example stent including a radioactive element coupled to a stent.

FIG. 10 shows an example stent 16 including one or more attachment members 24 configured to accept, receive, hold, grip and/or contain example strands 28. Similar to that described with respect to FIG. 4, stent 16 may include one or more attachment members 24 coupled or integrally formed with stent strut connectors 32.

Radioactive strands 28 may extend in a longitudinal direction across stent struts 26. Further, attachment members 24 may be connected to one or more struts 26 via strut connectors 32. Similar to that described above with respect to FIG. 4, attachment members 24 may be distributed along stent 16 in a variety of configurations. For example, FIG. 10 shows attachment members aligned longitudinally along stent 16 (which, in turn, aligns radioactive strands 28 longitudinally along stent 16). However, it is contemplated that attachment members 24 and/or radioactive strands 28 may be positioned in a variety of configurations with respect to the longitudinal axis of stent 16.

Figure 11:
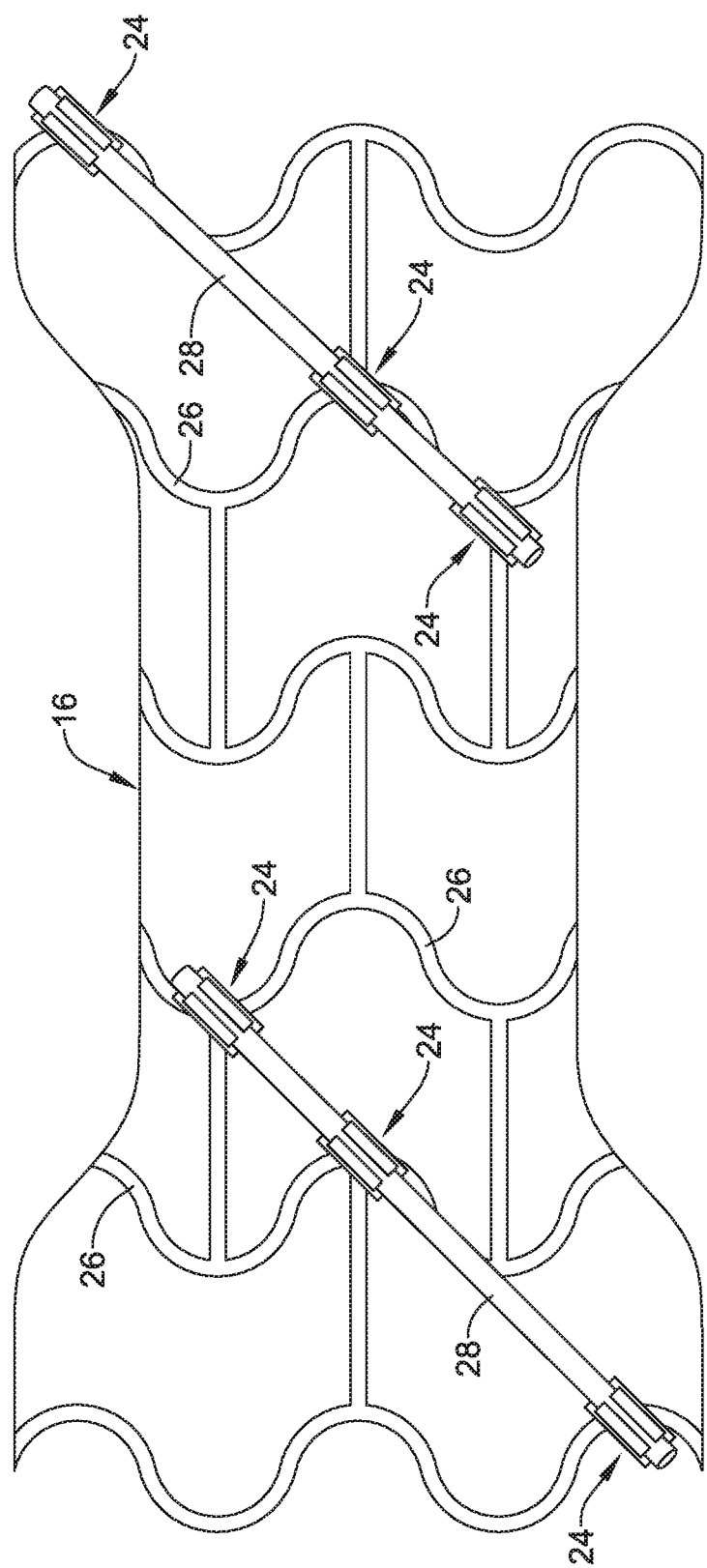
FIG. 11 is an example stent including a radioactive element coupled to a stent.

For example, FIG. 11 shows another example stent 16 (including attachment members 24 and radioactive strands 28) similar to that illustrated and described in FIG. 10. However, the attachment members 24 of FIG. 11 may be positioned at an angle across struts 26 of stent 16 (with respect the longitudinal axis of stent 16). It can be appreciated that any given strand 28 of FIG. 11 may extend at any angle and in a variety of different configurations with respect other individual strands 28 and/or stent 16.

The stent 16 depicted in FIG. 11 may represent a stent viewed in a flat pattern (e.g. a stent system as described herein cut along its longitudinal axis and laid flat). As can be seen in FIG. 11, two radioactive strands 28 are engaged across stent 16 in a helical arrangement. In some examples, the number of strands 28 in stent system may include more or less than two strands 28. For example, in some instances stent system 10 may include 1, 2, 3, 4, 5, 6, 7, 8, 9, 10, 15, 20 or more strands 28.

When viewed as a flat pattern, the two tubular members 18 are substantially parallel and spaced approximately equidistant from one another. Further, if the stent 16 shown in FIG. 11 were viewed as a cylinder (e.g., as it would be when delivered to a target site in the lumen), radioactive strands 28 would wrap around stent 16 as parallel helices. It is understood that example stent system 10 may include more or less than two radioactive strands 28.

The attachment members 24 described above with respect to FIGS. 10 and 11 may function in a similar fashion as the attachment members 24 described with respect to FIGS. 4-9. For example, the attachment members 24 may include one or more sides 18 that grip the radioactive strand 28. Further, the radioactive strands 28 may extend radially inward or radially outward from stent 16. Additionally, in some instances the radioactive strands 28 may weave from an inside surface of stent 16 to an outside surface of stent 16, then back to an inside surface of stent 16, and so on. In other words, radioactive members 28 may extend from an attachment member 24 positioned inside stent 16, through an opening in stent 16 to an attachment member 24 positioned outside stent 16, back to an attachment member 24 positioned inside stent 16 through another opening in stent 16, and so on.

Figure 12:
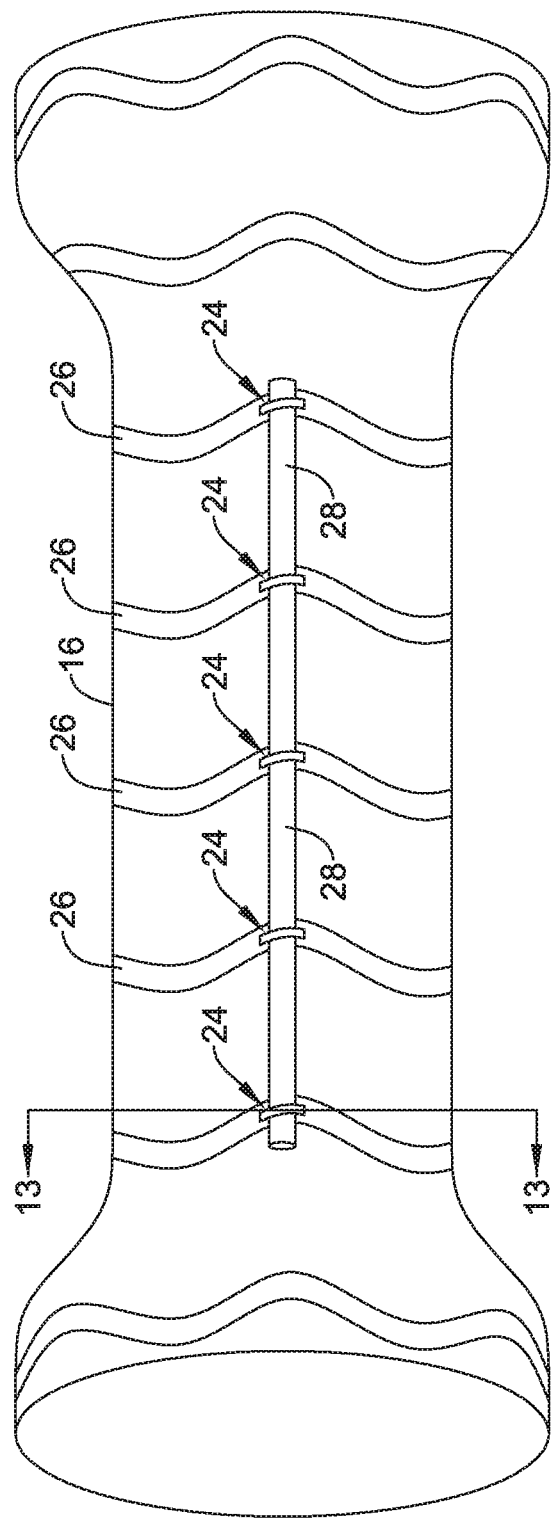
FIG. 12 is an example stent including a radioactive element coupled to a stent.

FIG. 12 shows another example attachment member 24 configured to couple radioactive element 28 to stent 16. While FIG. 12 shows a radioactive strand 28 coupled to stent 16, it is contemplated that the same attachment member 24 may function to grip and/or couple alternative radioactive elements (e.g., seeds 20) to stent 16. Further, as disclosed above, attachment members 24 may be configured in a variety of patterns and/or distributions along any portion (e.g., inside or outside) stent 16.

Figure 13:
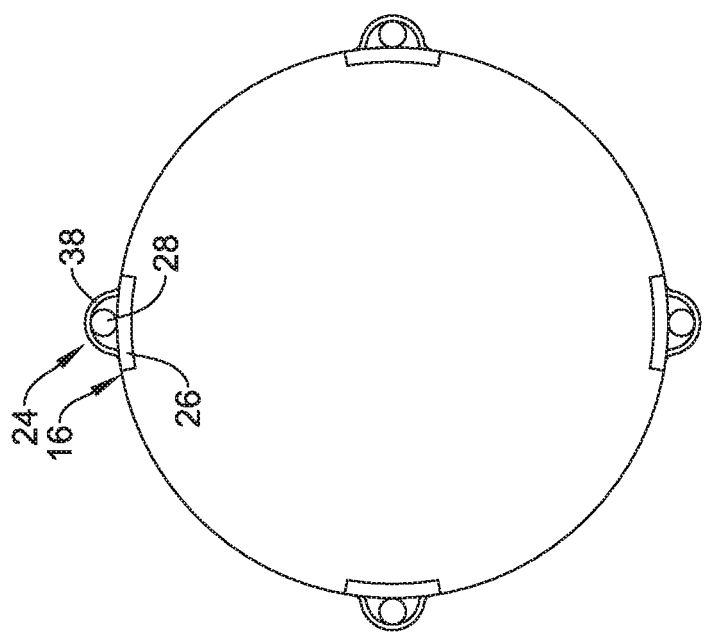
FIG. 13 is a cross section of example radioactive elements coupled to a stent.

FIG. 13 illustrates a cross section along line 13-13 of FIG. 12. As shown in FIGS. 12 and 13, in some examples attachment member 24 may be configured as a loop portion 38 extending outwardly from stent strut 26 and/or strut connector. Similar to the attachment member 24 described in FIGS. 2-9, loop portion 38 may be formed (e.g., laser cut) from stent strut 26 or strut connector. In it can be appreciated that in some instances loop portion 38 may be formed by cutting two parallel slots in stent strut 26 (or strut connector) and expanding the portion of stent strut 26 (or strut connector) between the two slots radially outward. As the loop portion 38 is expanded radially away from the surface of stent strut 26 (or strut connector), it may form an opening or aperture between the inside surface of loop portion 38 and the outside surface of stent strut 26 (or strut connector).

FIGS. 12 and 13 illustrate that radioactive elements (e.g., strands 28) may be positioned underneath the loop member 38 or extend through the opening/aperture formed by loop member 38. The opening/aperture through which the radioactive element extends may be sized such that it grips, holds and/or contains the radioactive element (e.g., seed 20 and/or strand 28) with sufficient force (e.g., inward radial force) to prevent the radioactive element from moving (e.g., sliding) with respect to the outer surface of stent 16.

It is contemplated that loop portion 38 may be formed into different shapes other than that depicted in FIGS. 12 and 13 while still maintaining sufficient inward radially force to prevent the radioactive element from moving (e.g., sliding) with respect to the outer surface of stent 16. For example, loop portion 38 may be substantially triangular, ovular, circular, round, rectangular, square, or the like.

Figure 14:
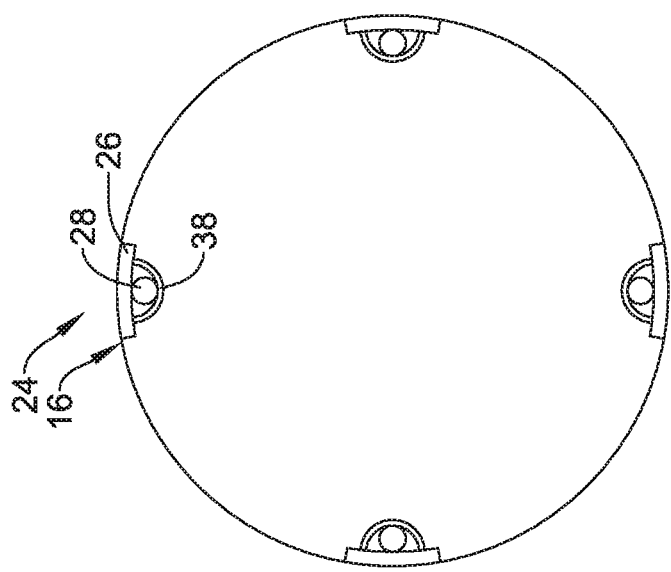
FIG. 14 is a cross section of example radioactive elements coupled to a stent.

Further, it is contemplated that loop portion 38 may extend inwardly from stent strut members 26. For example, FIG. 14 shows loop portions as described above in FIGS. 12 and 13 extending radially inward from the inner surface of stent strut 26. It can be appreciated that the radioactive elements 28 shown in FIG. 14 would extend along the inner surface of stent 16. In some examples, a push rod may be utilized during an example manufacturing process to invert the loop portions 38 to the position shown in FIG. 14.

Figure 15:
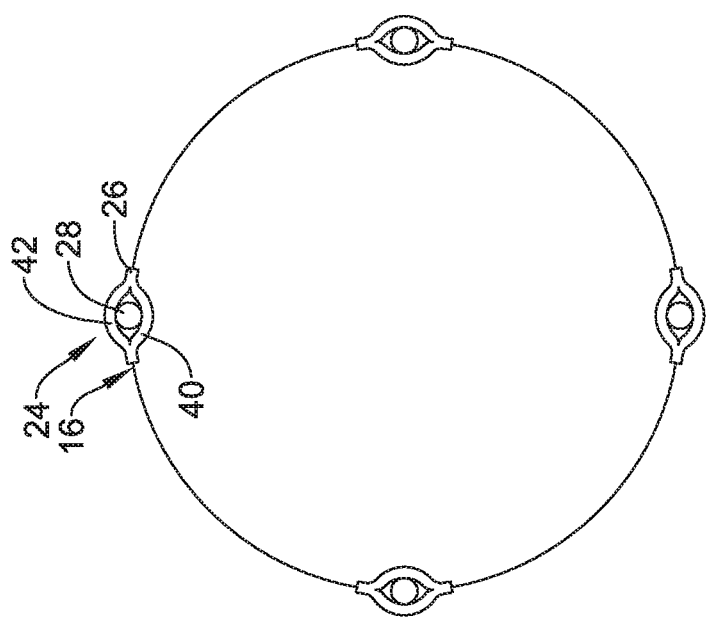
FIG. 15 is a cross section of example radioactive elements coupled to a stent.

FIG. 15 depicts another attachment member 24 having a loop portion 42 which extends radially outward and a loop portion 40 which extends radially inward from stent strut 26. FIG. 15 shows radioactive element 28 positioned between outwardly extending loop portion 42 and inwardly extending loop portion 40. As described with respect to FIGS. 12-14, loop portions 40/42 may be integrally formed from a portion of stent 16, such as stent strut 26 and/or strut connector. It can be appreciated that a laser cutting process may be utilized to form one or more cuts in strut 26 (or connector) such that an outwardly extending portion and an inwardly extending portion may be formed in a given stent strut 26 and/or connector.

It is noted that in other embodiments, the loop member 38 and/or loop portions 40/42 may be formed separately and subsequently attached to stent 16, such as stent strut 26 and/or strut connector.

Figure 16:
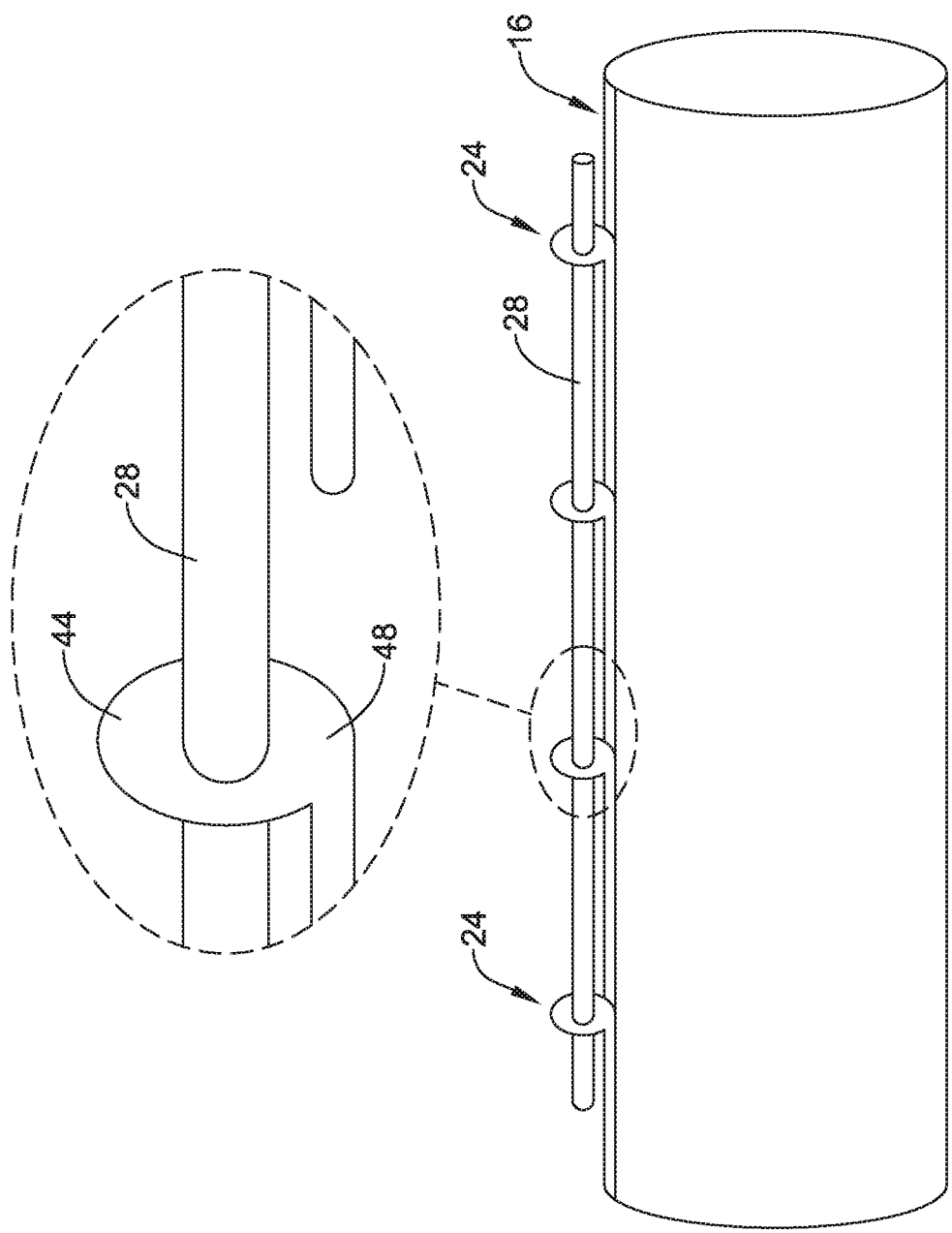
FIG. 16 illustrates an example stent including a tubular member coupled to an attachment member.

FIG. 16 shows another example attachment member 24 configured to couple radioactive element 28 to stent 16. While FIG. 16 shows a radioactive strand 28 coupled to stent 16, it is contemplated that the same attachment member 24 may function to grip and/or couple alternative radioactive elements (e.g., seeds 20) to stent 16. Further, as disclosed above, attachment members 24 may be configured in a variety as patterns and/or distributions along any portion (e.g., inside or outside) stent 16.

In some examples (such as that illustrated in FIG. 16), attachment members 24 may be formed (e.g., laser cut) into the stent geometry (e.g., formed integral with the tubular member forming the stent struts and/or connectors) and subsequently shaped (e.g., bent) into a second position in which the attachment member 24 is positioned to grip, accept, receive and/or hold a radioactive element (e.g., strand 28 and/or seed 20).

Figure 17:
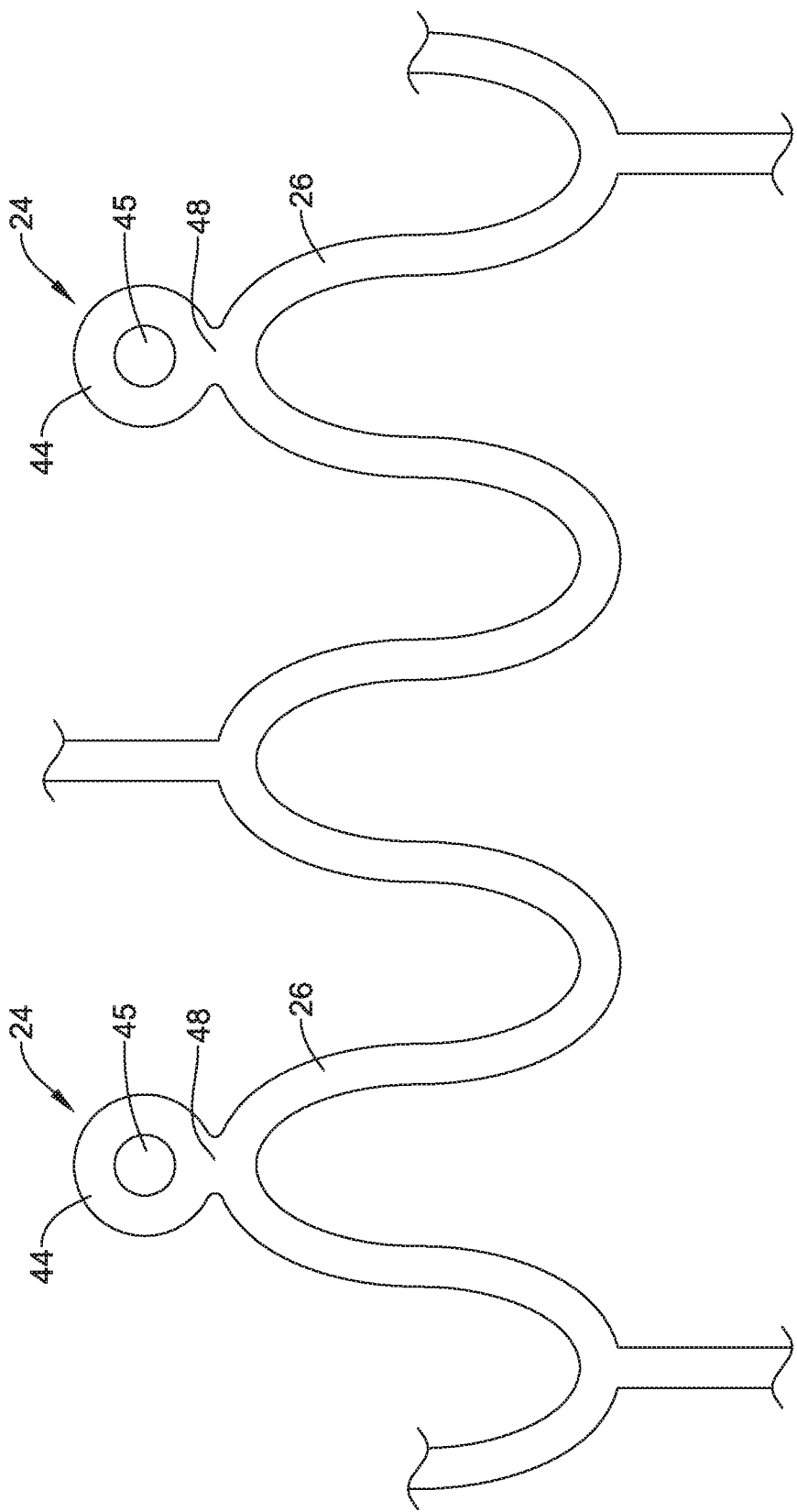
FIG. 17 is an example stent strut including an attachment member.
Figure 18:
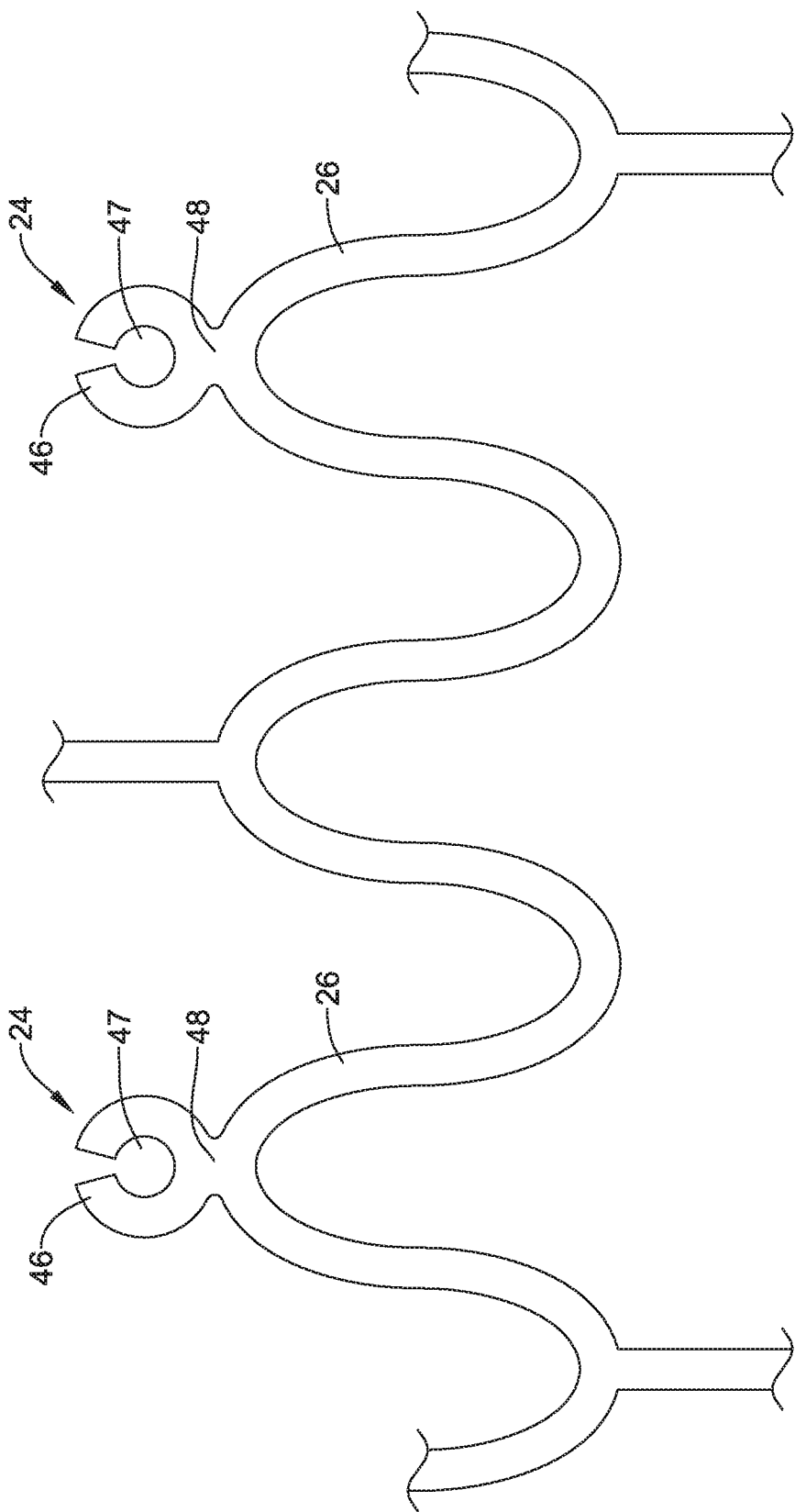
FIG. 18 is an example stent strut including an attachment member.

FIGS. 17 and 18 illustrate two example attachment members 24 designed to accept and/or grip a radioactive element (e.g., seed 20, strand 28, etc.). FIG. 17 shows attachment member 24 having two attachment portions 44, such as circular attachment portions, forming circular apertures 45. FIG. 18 shows two attachment members 24 having semi-circular attachment portions 46 having two attachment openings 47, with a slot opening into the openings 47 from an exterior of the attachment members 24. In addition, the attachment members depicted in FIGS. 17 and 18 both include a neck region 48 extending from the stent strut 26 (or other region of the stent structure).

The shapes of attachment portions 44/46 are not intended to be limiting. Rather, it is contemplated that attachment portions 44/46 may include a variety of different shapes and/or geometries designed to accept a radioactive element (e.g., seed 20, strand 28). Further, while FIGS. 17 and 18 show two individual attachment portions 44/46 extending from stent strut 26, it is contemplated that stent 16 may include more or less than two individual attachment portions 44/46. For example, stent 16 may include 1, 2, 3, 4, 5, 6, 7, 8, 9, 10, 15, 20 or more attachment portions 44/46 distributed in a variety of configurations and/or distributions along stent 16.

As discussed above, attachment portions 44/46 may be formed during the same manufacturing process that forms other portions of stent 16. For example, attachment portions 44/46 may be laser cut during the formation of stent struts 26 from a tubular member. Further, as shown in FIGS. 17 and 18, attachment portions 44/46 may be formed from stent strut 26.

In some instances, after attachment portions 44/46 have been formed by an initial manufacturing process, a second manufacturing process may transform the attachment portions 44/46 from a first position (e.g., a position in which portions 44/46 are substantially flush with the outer surface of stent 16) to a second position in which attachment portions 44/46 are substantially perpendicular to the outer surface of stent 16. In some instances, portions 44/46 may be bent from the first position to the second position. Further, portions 44/46 may be bent along neck region 48 (shown in FIGS. 17 and 18).

FIG. 16 shows attachment portions 44/46 in a second position in which they are substantially perpendicular to stent 16. As shown in the detailed view of FIG. 16, attachment portions 44 may be bent at neck region 48 such that attachment portions 44 extend radially outward from the outer surface of stent 16. FIG. 16 further illustrates radioactive element (e.g., strand 28) extending through the apertures 45/47 (shown in FIGS. 17 and 18) of attachment members 44. The apertures 45/47 are designed to grip, hold and/or couple the radioactive element (e.g., strand 28) adjacent to stent 16.

Figure 20:
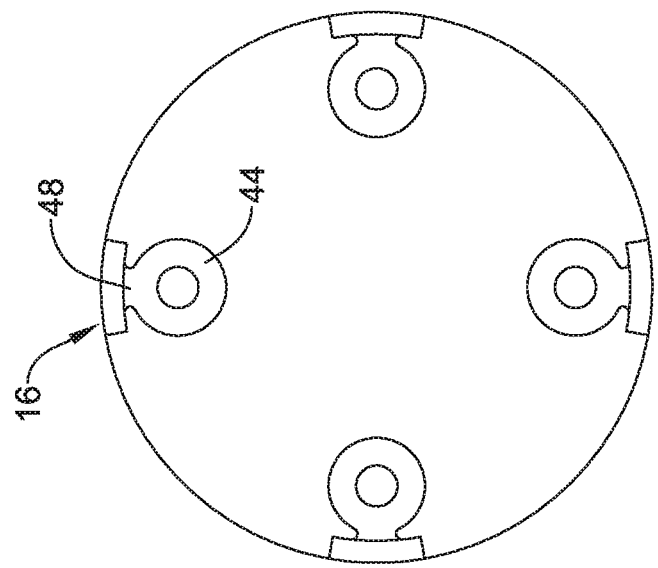
FIG. 20 is a cross section of a stent strut including an attachment member.
Figure 19:
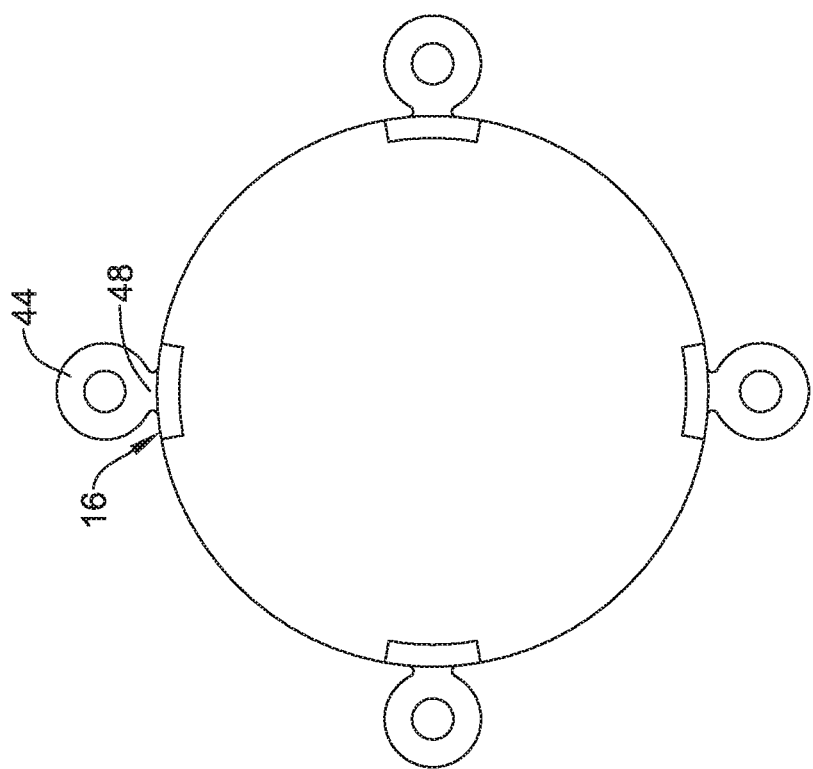
FIG. 19 is a cross section of a stent strut including an attachment member.

In some instances it may be desirable for attachment members 44/46 to extend radially inwardly from stent 16. For example, FIGS. 19 and 20 show example cross sections of the attachment members 44 extending outwardly and inwardly, respectively, from the surface of stent 16. For example, FIG. 19 shows a cross section of the attachment members 44 extending outwardly from the outer surface of stent 16, while FIG. 20 shows a cross section of the attachment members 44 extending inwardly from the inner surface of stent 16. It can be appreciated that the radioactive elements 28 shown in FIG. 20 would extend along the inner surface of stent 16 when the attachment members 44 bend radially inward from an inner surface of stent 16. Additionally, both FIGS. 19 and 20 depict attachment members 44 being bent along the neck region 48.

Figure 21:
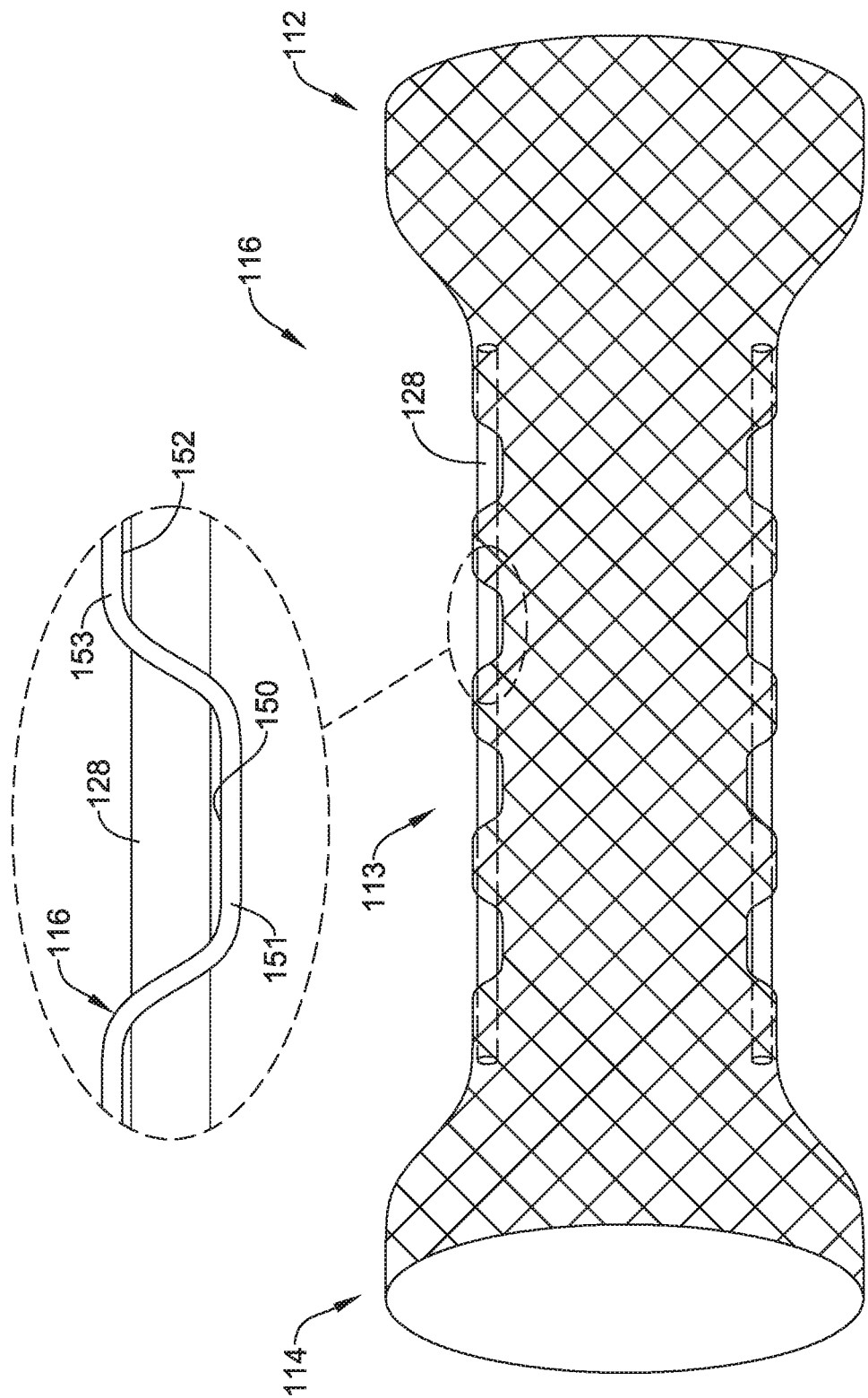
FIG. 21 is an example stent including tubular members coupled to a stent.

FIG. 21 shows another example radioactive element (e.g., strand 128) coupled to stent 116. Further, as shown in FIG. 21, stent 116 may have a proximal portion 112, a distal portion 114 and an intermediate portion 113. As shown, the proximal and distal portions 112/114 of stent 116 may be flared or enlarged relative to the intermediate portion 113, such that the proximal and distal portions 112/114 have a larger overall diameter than intermediate portion 113. In some instances, the shape of stent 116 may resemble that of a "dog bone," for example.

Additionally, intermediate portion 113 may include one or more strut members having an inner diameter and an outer diameter than is different from (e.g., greater than or less than) one or more other strut members. For example, the detailed view of FIG. 21 shows example strut 151 having an outer surface 150 and example strut 153 having an inner surface 152. Further, FIG. 21 shows that the diameter of inner surface 152 is greater than the diameter of outer surface 150. It can be appreciated that a variety of different stent strut dimensions (e.g., diameters) may be utilized to create numerous geometrical relationships among stent struts.

FIG. 21 further illustrates example radioactive element 128 extending between the stent struts of stent 116. For example, the detailed view of FIG. 21 shows radioactive element 128 positioned between stent strut 151 and stent strut 153. In the example shown, radioactive element 128 is positioned such that it contacts the outer surface 150 of stent strut 151 and the inner surface 152 of stent strut 153. In other words, radioactive element 128 may be "sandwiched" in the opening and/or spacing between the offset diameters of stent struts 151 and 153. As shown in FIG. 21, stent 116 may include more than one location along stent 116 in which radioactive element 128 may be positioned between stent struts.

In some instances, the examples discussed herein may further include one or more "intensity modulation filters" (also referred to herein as "shields") designed to reduce and/or modulate the amount of radiation delivered by a radioactive element. For example, one or more shield may be placed between a radioactive element (e.g., seed 20 and/or strand 28) and the vessel wall (e.g. targeted tissue) in order to modulate the amount of radiation reaching the tissue.

Figure 22:
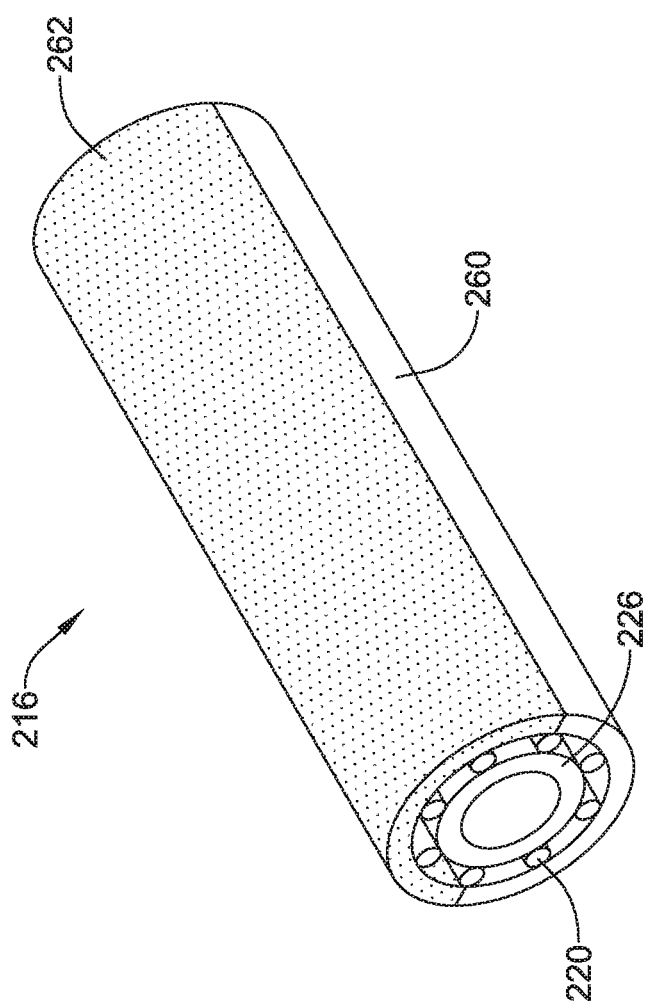
FIG. 22 is an example stent including a shield.

FIG. 22 shows an example stent 216 including stent scaffold 226 and stent covering 260. Further, FIG. 22 illustrates radioactive elements 220 extending along stent 216. While FIG. 22 depicts radioactive elements 220 positioned radially outward of stent scaffold 226, it is contemplated that radioactive elements 220 may be coupled to stent scaffold 226 according to any of the examples disclosed herein. For example, stent 216 may include radioactive seeds and/or strands coupled to attachment members according to any of the examples disclosed herein.

As shown in FIG. 22, a portion of covering 260 may include shield 262 extending along stent 216. In other words, shield 262 may be integrally formed with covering 260. For example, shield 262 may define a portion of the stent wall. In some instances, shield 262 may be applied to stent 216 by dipping or spraying. Additionally, it is contemplated that shield 262 may extend around the circumference of stent 216 to more or less than that depicted in FIG. 22. For example, shield 262 may extend from about 75-100% of the circumference of stent 216, or about 50-75% of the circumference of stent 216, or about 25-50% of the circumference of stent 216, or about 0-25% of the circumference of stent 216.

Figure 23:
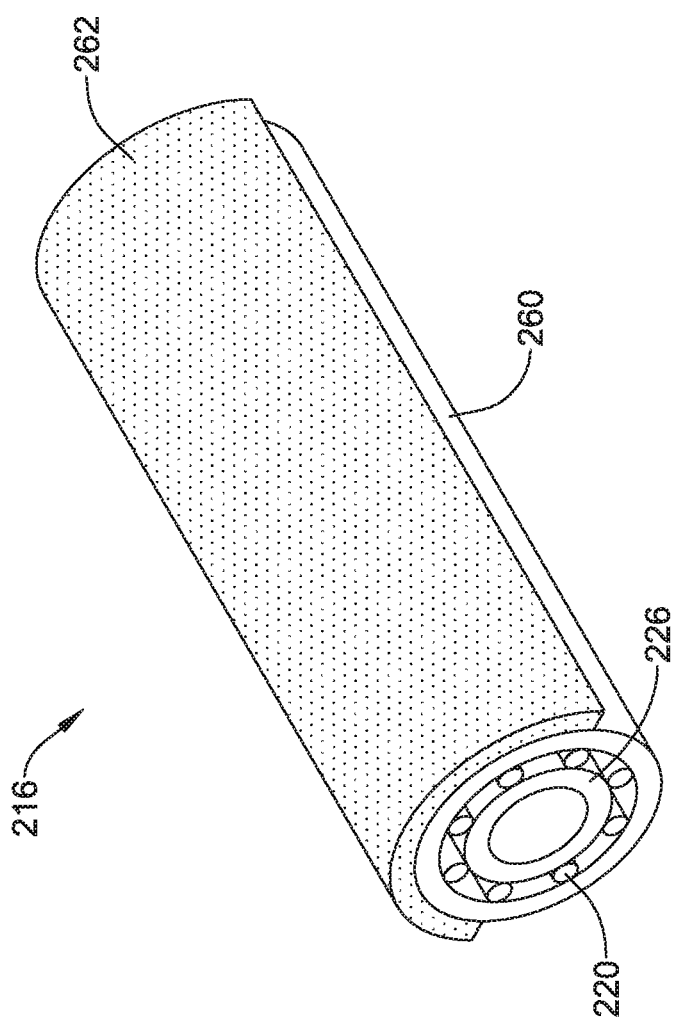
FIG. 23 is an example stent including a shield positioned on the outside of the stent.

FIG. 23 shows that one or more shields 262 may be placed on the outer surface of stent 216, thereby modulating the radiation delivered by radioactive elements positioned inward of shields 262. For example, FIG. 23 shows that shield 262 may be positioned on top of the stent covering 260 (e.g., stent wall). Similarly to that discussed with respect to FIG. 22, shield 262 may be applied to stent 216 by dipping or spraying. Additionally, it is contemplated that shield 262 may extend around the circumference of stent 216 to more or less than that depicted in FIG. 23. For example, shield 262 may extend from about 75-100% of the circumference of stent 216, or about 50-75% of the circumference of stent 216, or about 25-50% of the circumference of stent 216, or about 0-25% of the circumference of stent 216.

Figure 24:
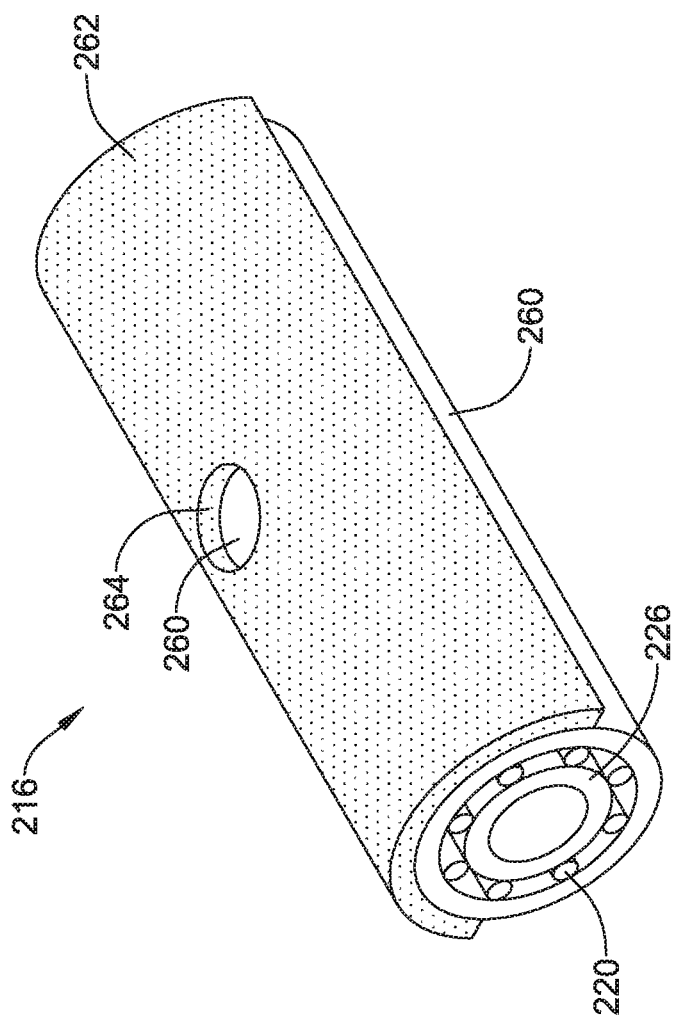
FIG. 24 is an example stent including a shield having an opening.

FIG. 24 illustrates the stent disclosed in FIGS. 22 and 23 having an aperture or opening 264 formed in the stent covering 260 (e.g., stent wall) and/or shield 262. Aperture 264 may include a variety of shapes and/or configurations. For example, aperture 264 may be defined as round, square, rectangular, ovular, triangular or the like. In some examples, aperture 264 may extend fully or partially through shield 262 while not extending through stent covering 260. In other examples, aperture 264 may extend fully or partially through both shield 262 and stent covering 260.

Shield 262 may be constructed out of a variety of materials including metal, metallic powder, polymer, etc. or any other material or combination of materials that attenuate radiation. In some instances the shield material may be placed inside a polymer. For example, the shields may include tungsten powder inside silicone. Further, in some instances, shield 262 may be of varying thickness. In some examples the thickest portion of shield 262 may include that portion of the shield 262 that is closest to the radioactive elements. Further, the thickness may taper (and become thinner) at the shield extremities.

Materials that may be used for the various components of stent system 10 and the various examples disclosed herein may include those commonly associated with medical devices. For simplicity purposes, the following discussion makes reference to stent system 10. However, this is not intended to limit the devices and methods described herein, as the discussion may be applied to other similar systems and/or components of stent systems or devices disclosed herein.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
a stent having a tubular scaffold including an inner surface and an outer surface and first and second opposing ends;
a plurality of attachment members coupled to the tubular scaffold, at least a first attachment member of the plurality of attachment members being formed from the tubular scaffold by cutting lines through the tubular scaffold and bending a portion of the tubular scaffold adjacent the cut lines to form the first attachment member; and
a radioactive element;
wherein the first attachment member is formed between the first and second ends of the stent and imparts a compressive force upon the radioactive element to couple the radioactive element to the first attachment member.

2. The medical device of claim 1, wherein the radioactive element further comprises an axially elongated radioactive seed.

3. The medical device of claim 1, wherein the first attachment member includes a base, and the portion of the tubular scaffold bent adjacent the cut lines includes a first grip member and a second grip member, wherein the first and second grip members extend away from the base member.

4. The medical device of claim 3, wherein the radioactive element is positioned between the first and second grip members.

5. The medical device of claim 4, wherein the radioactive element is positioned radially outward from the base member.

6. The medical device of claim 5, wherein the first and second grip members are configured to compress the radioactive element against the base member.

7. The medical device of the claim 1, wherein the tubular scaffold comprises a first strut and a second strut longitudinally spaced from the first strut, and wherein the first attachment member is positioned between the first strut and the second strut.

8. The medical device of claim 7, further comprising a first connector having a first end coupled to the first strut and a second end coupled to the second strut, and wherein the first attachment member is formed from the first connector.

9. The medical device of claim 1, wherein the radioactive element includes a radioactive strand, and wherein the radioactive strand extends from the first attachment member to the second attachment member.

10. The medical device of claim 1, further comprising a radioactive shield, wherein the radioactive shield is configured to modulate radioactive energy released from the radioactive element.

11. The medical device of claim 1, wherein the first attachment member extends radially outward from the outer surface of the tubular scaffold.

12. The medical device of claim 1, wherein the portion of the tubular scaffold bend adjacent the cut lines is bent inward toward a lumen of the stent.

13. A medical device, comprising:
a stent including a monolithic tubular scaffold having first and second opposing ends, the scaffold including a plurality of integrally formed struts defining one or more interstices therebetween;
a plurality of attachment members coupled to the monolithic tubular scaffold, at least a first attachment member of the plurality of attachment members being formed from the monolithic tubular scaffold by cutting lines through the monolithic tubular scaffold and bending a portion of the monolithic tubular scaffold adjacent the cut lines to form the first attachment member; and
a radioactive element disposed along the attachment member;
wherein the first attachment member is formed between the first and second ends of the stent and imparts a compressive force upon the radioactive element to removably couple the radioactive element to the first attachment member.

14. The medical device of claim 13, further comprising a second attachment member, and wherein the second attachment member is circumferentially spaced from the first attachment member.

15. The medical device of claim 13, wherein the radioactive element includes a radioactive seed, a radioactive strand, or both.

16. The medical device of claim 13, further comprising a radioactive shield, wherein the radioactive shield is configured to modulate radioactive energy released from the radioactive element.

17. The medical device of claim 13, wherein the first attachment member includes a base, a first grip member and a second grip member, wherein the first and second grip members extend away from the base member.

18. The medical device of claim 17, wherein the radioactive element is positioned between the first and second grip members.

19. A medical device, comprising:
a stent having a tubular scaffold including an inner surface and an outer surface, the tubular scaffold including first and second struts and a connector extending between the first and second struts;
a plurality of attachment members coupled to the connector, at least a first attachment member of the plurality of attachment members being formed from the connector by cutting lines through the connector and bending a portion of the connector adjacent the cut lines to form the first attachment member, wherein the first attachment member includes a first gripping portion and a second gripping portion extending from a base; and
a radioactive element positioned between the first and second gripping portions, wherein the radioactive element extends radially outward from the base.

20. The medical device of claim 19, wherein the first gripping portion and the second gripping portion direct a compressive force upon the radioactive element to couple the radioactive element to the base.

* * * * *